United States Patent
Weissleder et al.

(12) 
(10) Patent No.: US 6,511,967 B1
(45) Date of Patent: Jan. 28, 2003

(54) USE OF AN INTERNALIZING TRANSFERRIN RECEPTOR TO IMAGE TRANSGENE EXPRESSION

(75) Inventors: Ralph Weissleder, Charlestown, MA (US); James P. Basilion, Brookline, MA (US); Ennio Antonio Chiocca, Wakefield, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/552,993

(22) Filed: Apr. 21, 2000

Related U.S. Application Data
(60) Provisional application No. 60/130,794, filed on Apr. 23, 1999.

(51) Int. Cl.$^7$ .......................... A61K 31/70; C12Q 1/68; C07H 21/02; C07H 21/04
(52) U.S. Cl. ........................... 514/44; 435/6; 536/23.1; 536/23.4
(58) Field of Search ............................. 514/44, 16, 17, 514/18; 424/1.73; 435/6; 530/350, 307; 534/10; 536/23.1, 23.4

(56) References Cited

U.S. PATENT DOCUMENTS
5,492,814 A * 2/1996 Weissleder .................. 435/725

OTHER PUBLICATIONS
AMoore et al.,BBA, "Measuring transferrin receptor gene expression by NMR imaging," 1998, 1402:239–249.*
S Liu et al., Chem Rev., "99mTc–Labeled Small Peptides as Diagnostic Radiopharmaceuticals," 1999, 99, 2235–2268.*
LL Muldoon et al., American Journal of Pathology, "Comparison of Intracerebral Inoculation and Osmotic Blood–Brain Disruption for Delivery of Adenovirus, Herpersvirus, and Iron Oxide Particles to Normal Rat Brain," Dec. 1995, vol. 147, No. 6,pp. 1840–1851.*
AM Williams et al., Journal of Biological Chemistry, "Region of the C–terminal Portion of the Human Transferrin Receptor contains as Asparagine–linked Glycosylation Site Critical for Receptor Structure and Function," 1993,vol. 268, No. 17, pp. 12780–12786.*
R Weissleder et al., AJR, "MR Receptor Imaging:Ultrasmall Iron Oxide Particles Targeted to Asialoglycoprotein Receptors," Dec. 1990, 155: 1161–1167.*
Koretsky et al., "Genetic Control of MRI Contrast by Expression of the Transferrin Receptor," Int. Soc. Magn Resonan. Med. NY, p. 5471 Apr. 27 (1996).
Koretsky et al., "NMR Detection of Creatine Kinase Expressed in Liver of Transgenic Mice: Determination of Free ADP Levels," Proc. Natl. Acad. Sci. (USA) 87, p. 3112–3116 (1990).
Kresse et al., "Targeting of Ultrasmall Superparamagnetic Iron Oxide (USPIO) Particles to Tumor Cells In Vivo by Using Transferrin Receptor Pathways," MRM, vol. 40, p. 236–242 (1998).
Liu et al., "$^{99m}$Tc–Labeled Small Peptides as Diagnostic Radiopharmaceuticals", Chem. Rev., vol. 99, p. 2235–2268 (1999).
Moore et al., "Measuring Transferring Receptor Gene Expression by NMR Imaging," Biochimica et Biophysica Acta, vol. 1402, p. 239–249 (Apr. 24, 1998).
Roman et al., "Functional Equivalence of Creatin Kinase isoforms in Mouse Skeletal Muscle," J. Biol. Chem. 272, p. 17790–17794 (1997).
Weissleder et al., "In Vivo Magnetic Resonance Imaging of Transgene Expression," Nature Medicine, vol. 6, No. 3, p. 351–354 (Mar. 2000).
Shen, et al., "Magnetically Labeled Secretin Retains Receptor Affinity to Pancras Acinar Cells," Bioconjugate Chem., vol. 7, No. 3, pp. 311–316.
Wang, et al., "A Hybrid Herpesvirus Infectious Vector Based on Epstein–Barr Virus and Herpes Simplex Virus Type 1 for Gene Transfer into Human Cells In Vitro and In Vivo," Journal of Virology, Dec. 1196, p. 8422–8430.
Weissleder, et al., "MR Receptor Imaging: Ultrasmall Iron Oxide Particles Targeted to Asialoglycoprotein Receptors," AJR 155:1161–1167, Dec. 1990.

* cited by examiner

Primary Examiner—Deborah Crouch
Assistant Examiner—Joseph Woitach
(74) Attorney, Agent, or Firm—Fish & Richardson PC

(57) ABSTRACT

Cells can be imaged, e.g., in vivo, in an animal or human subject by introducing into the cells a nucleic acid encoding an internalizing receptor, administering to the animal or human subject a reporter complex including one or more receptor-specific reporter moieties linked to one or more reporter groups, such as magnetic particles, and detecting the reporter complex, e.g., using magnetic resonance imaging, and thus detecting the cells. If a specific gene is expressed in a constant, known ratio compared to expression of the receptor, the expression of that gene can be monitored by detecting the reporter complex, and thus, concomitantly, expression of the internalizing receptor and the specific gene.

27 Claims, 12 Drawing Sheets

MR imaging

Tf-MION

SEQUENCE LISTING

```
<160> NUMBER OF SEQ ID NOS: 6

<210> SEQ ID NO 1
<211> LENGTH: 6
<212> TYPE: PRT
<213> ORGANISM: Homo sapiens

<400> SEQUENCE: 1

Phe Asp Asn Pro Val Tyr
 1              5

<210> SEQ ID NO 2
<211> LENGTH: 4
<212> TYPE: PRT
<213> ORGANISM: Homo sapiens

<400> SEQUENCE: 2

Tyr Thr Arg Phe
 1

<210> SEQ ID NO 3
<211> LENGTH: 6
<212> TYPE: PRT
<213> ORGANISM: Homo sapiens

<400> SEQUENCE: 3

Asp Lys Gln Thr Leu Leu
 1              5

<210> SEQ ID NO 4
<211> LENGTH: 17
<212> TYPE: PRT
<213> ORGANISM: Homo sapiens

<400> SEQUENCE: 4

Trp Gln Glu Glu Cys Pro Ser Asp Ser Glu Glu Asp Glu Gly Arg Gly
 1              5                   10                  15

Arg

<210> SEQ ID NO 5
<211> LENGTH: 4
<212> TYPE: PRT
```

```
<213> ORGANISM: Homo sapiens

<400> SEQUENCE: 5

Lys Arg Phe Tyr
 1

<210> SEQ ID NO 6
<211> LENGTH: 10
<212> TYPE: PRT
<213> ORGANISM: Homo sapiens

<400> SEQUENCE: 6

Glu Val Val Asp Ile Met Arg Val Asn Val
 1               5                  10
```

USE OF AN INTERNALIZING TRANSFERRIN RECEPTOR TO IMAGE TRANSGENE EXPRESSION

CROSS-REFERENCE TO RELATED APPLICATION

This application claims benefit from U.S. Provisional Patent Application Ser. No. 60/130,794, file on Apr. 23, 1999, which is incorporated herein by reference in its entirety.

FIELD OF THE INVENTION

This invention relates to imaging of cells and of gene expression.

BACKGROUND

A number of different approaches to imaging cells and gene expression have been investigated using either optical imaging techniques, e.g., using green fluorescent protein, bioluminescence, or near infrared fluorescence, or nuclear imaging techniques. However, these techniques may have limited depth penetration (optical techniques) or spatial resolution (nuclear techniques). Magnetic resonance (MR) imaging has also been used, and recent advances in MRI, and in particular MR microscopy, have led to improved image resolution. However, compared to current optical and nuclear techniques, molecular probe detection by MR is several magnitudes less sensitive.

SUMMARY OF THE INVENTION

The invention is based on the discovery that cells can be imaged, e.g., in vivo in an animal or human by introducing into the cells a nucleic acid encoding an internalizing receptor, administering to the animal or human a reporter complex including one or more receptor-specific reporter moieties linked to one or more reporter groups, such as magnetic particles, and detecting the reporter complex, e.g., using magnetic resonance imaging, and thus detecting the cells. If a specific gene is expressed in a constant, known ratio compared to expression of the receptor, e.g., if expression of the two genes is linked, the expression of that gene can be monitored by detecting the reporter complex, and thus, concomitantly, expression of the internalizing receptor and the specific gene.

Accordingly, the invention generally features a methods of imaging expression of a specific gene, e.g., a therapeutic gene such as one that encodes an enzyme, in vivo in a subject, by introducing a nucleic acid encoding an internalizing receptor and the specific gene into cells in the subject; administering to the subject a reporter complex comprising a receptor-specific moiety and a reporter group, wherein the reporter complex binds to the internalizing reporter; and imaging the subject to monitor the reporter complex as an indication of gene expression. For example, the nucleic acid encoding the internalizing receptor can be in a viral or nonviral vector. The imaging can be, for example, magnetic resonance imaging, NMR spectroscopy, or nuclear imaging.

In a specific example, the internalizing receptor is a transferrin receptor, and the reporter complex comprises transferrin and one or more magnetic, paramagnetic, or superparamagnetic nanoparticles. In another example, reporter group is a magnetic particle, an optically detectable molecule, or a radioisotope. In addition, the internalizing receptor can be genetically modified, e.g., to alter recycling of the receptor, internalization, ligand affinity, or receptor half-life within the cell.

In certain embodiments, the reporter complex includes one or more cross-linked iron oxide nanoparticles (CLIOs) or monocrystalline iron oxide nanoparticles (MIONs).

In another aspect, the invention features nucleic acid constructs including a nucleic acid sequence encoding an internalizing receptor, e.g., a transferrin receptor; and a specific gene, such as a therapeutic gene, for example one that encodes an enzyme that metabolizes a drug. The construct can be non-down-regulatable. The gene can also encode a gene product, e.g., for replacement gene therapy, such as the p53 gene. The construct can further include one or more regulatory sequences. For example, the regulatory sequence can include a promoter (e.g., a bicistronic construct) or two promoters, that can be the same or different. In certain embodiments, the promoter induces expression without regulation by environmental conditions within a cell. In certain embodiments, the nucleic acid encoding the receptor can be genetically modified.

The invention also features a viral or nonviral vector, or other nucleic acid delivery vehicle, that includes the new nucleic acid constructs.

In another aspect, the invention also features a reporter complex including one or more internalizing receptor-specific moieties and one or more reporter groups, e.g., magnetic, paramagnetic, or superparamagnetic particles, e.g., monocrystalline iron nanoparticles (MIONs) or cross-linked dextran coated iron oxide nanoparticle (CLIOs), or optically detectable molecules (e.g., fluorescent molecules (e.g., FITC or rhodamine), near infrared molecules (e.g., Cy5), or autoquenching molecules), or radioisotopes (e.g., iodine-125, Tc-99, In-111, or Fe-59). The complex can also include a linker molecule that connects the receptor-specific moiety to the reporter group. The linker is bi- or multi-functional and thus has at least two reactive groups that bind to the reporter group and the receptor-specific moiety. The linker can provide a spacer between the linked reporter group and the moiety.

In another aspect, the invention features a method of inducing cells to internalize magnetic particles, by introducing into the cells a nucleic acid encoding an internalizing receptor; and contacting the cells with a reporter complex comprising a receptor-specific moiety and a reporter group, whereby the moiety binds to the receptor and the complex is moved into the cell carrying the reporter group. The reporter group can be a magnetic particle, an optically detectable molecule, or a radioisoptope.

The invention also features transgenic animals and cell lines that include the new nucleic acid constructs. In addition, the invention includes imaging kits that contain the new nucleic acid constructs and reporter complexes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides numerous advantages. For example, the invention provides real time imaging of gene expression in vivo at high spatial resolutions, which enables the study of both endogenous and exogenous (e.g., gene therapy, such as therapeutic, e.g., short-term, gene therapy or long-term, replacement gene therapy) gene expression in live animals and in human clinical studies. In addition, the new methods are noninvasive, and enable repeated longitudinal studies within same animal or human patient.

Other features and advantages of the invention will be apparent from the following detailed description, and from the claims.

DETAILED DESCRIPTION

Figure 1:
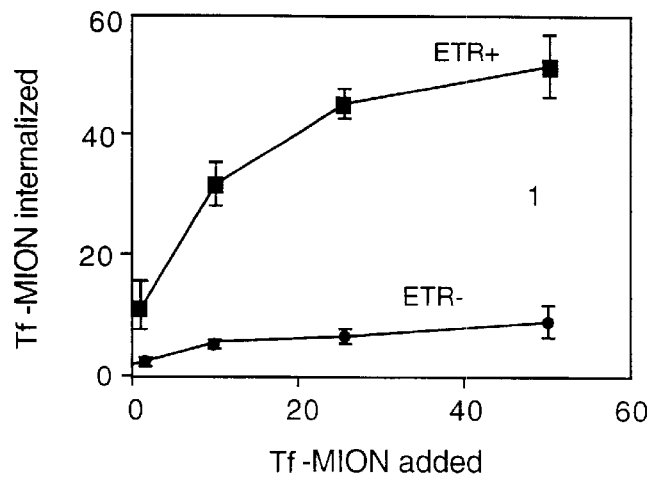
FIG. 1 is a graph illustrating the 5 fold increase in cell uptake of a receptor targeted reporter complex (transferrin-MION; Tf-MION) in cells expressing the receptor (ETR+), compared to uptake of the same complex by cells that do not express the receptor (ETR−).
Figure 2:
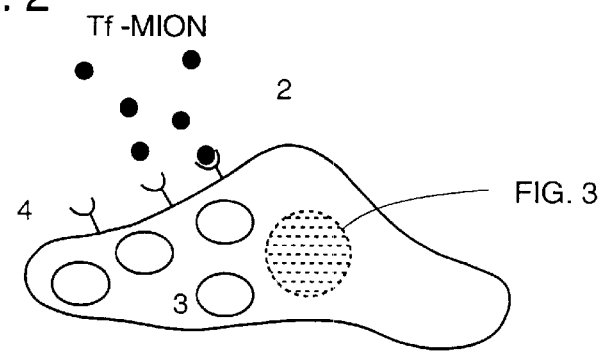
FIG. 2 is a schematic diagram of reporter complexes bound to internalizing receptors on the surface of a cell, and internalized reporter complexes stored within compartments within the cell.

The new methods reported here rely on the expression of an internalizing receptor that is, or is engineered to be, highly, and preferably non-regulatably, expressed, and that shuttles targeted magnetic particles into cells (via conjugation to specific receptor ligands), which in turn alter their relaxivity and thus serve as detectible markers or reporters.

Some native, endogenous internalizing receptors, such as native human transferrin receptor, may not be suitable for use in the new methods, if they are not expressed at a sufficiently high level, or, as in the case of the native human transferrin receptor (TfR), their expression is downregulated under conditions most suitable for imaging (increased iron concentration within the cell). Thus, certain internalizing receptors, such as the TfR, need to have regulatory sequences removed or altered and instability elements removed, e.g., to create an engineered transferrin receptor (ETR), to ensure that they will be positively expressed at sufficiently high levels under all circumstances. Alternatively, where the iron level may change receptor expression, magnetic probes or ligands synthesized such that iron is not delivered to the cell in a way that will affect the physiology or iron metabolism of the cells should be employed. For example (but not limited to), these magnetic probes could be MIONs or conjugated MIONs, which have been demonstrated not to alter TfR levels (Moore et al., *Biochemica Biophysica Acta,* 1402:239–249, 1998).

The new methods hold promise not only for high-resolution in vivo imaging but also for repeated sampling. The detection threshold of imaging gene expression by MR imaging depends on the amount of cell internalized iron and spatial resolution. According to the new methods, up to $8\times10^6$ nanoparticles can be internalized into ETR+ cells within one hour, which is theoretically sufficient to detect single cells using microscopic MR imaging. In addition, because many intracellular magnetic particles, such as MIONs, are biodegradable, repeated imaging can theoretically be performed to assess transgene expression over time.

The new reporter complexes can also be used to image diseased or abnormal tissues, such as tumors, e.g., breast tumors, that exhibit higher than normal levels of internalizing receptors, for example, because of their increased rate of proliferation compared to normal cells. In such cases, the diseased tissue, e.g., tumor, cells have more internalizing receptors on their surface than normal cells, and the new reporter complexes can be administered to the patient without the need for first administering a nucleic acid encoding an internalizing receptor. One such receptor is the HER2 receptor. Other receptors that are overexpressed on cancers or other abnormally growing cells include, but are not limited to, the LDL receptor, the IGF-1 receptor, the TfR, the CI Man-6-P receptor, Lamp-1, the bombesin receptor, and the folate receptor.

General Methodology

The new methods can be achieved by obtaining a nucleic acid encoding an internalizing receptor and introducing this nucleic acid into a cell in a construct or vector that causes the nucleic acid to be expressed in the cells. This construct can be used for imaging the cells. Alternatively, the construct includes a desired therapeutic gene whose expression is to be monitored, or the nucleic acid and the desired gene can both inserted into another construct or vector, such as an amplicon.

In one embodiment, the desired gene, e.g., a therapeutic gene, and the nucleic acid encoding the receptor are operably linked in a single expression vector, e.g., under the control of the same promoter, so that when the receptor is expressed, the desired gene is necessarily also expressed. Alternatively, one expression vector or construct can be designed to drive the expression of two gene products using two promoters (either the same or different promoters can be used). In another alternative, two constructs can be prepared that are designed to express the desired gene and the nucleic acid encoding the receptor in a constant ratio.

The receptor/gene nucleic acid construct is then introduced into specific cells or types of cells of a subject animal (e.g., a mammal such as a dog, cow, horse, cat, mouse, rat, hamster, gerbil, or monkey) or human, by various known techniques, such as with a viral or nonviral transfer vector, gene gun, gold particle injection, liposome, or by electroporation.

Next, a reporter complex is obtained that includes a receptor-specific reporter moiety, e.g., a ligand, that specifically binds to the receptor, and a reporter group, such as a magnetic particle, e.g., a superparamagnetic, ferromagnetic, or paramagnetic particle or nanoparticle. The reporter can also be an optical reporter, such as a fluorescent molecule (e.g., FITC or rhodamine), a near infrared dye such as Cy5, or a radioisotope reporter such as I-125, Tc-99, In-111, or Fe-59. This reporter complex is administered to the animal or human, e.g., by local injection or systemically, in an amount effective to achieve a detectable level of the reporter group, e.g., magnetic nanoparticles, in the cells, i.e., an amount effective to change the signal intensity, e.g., the relaxivity, of the cells, and imaging the animal or human subject to monitor the reporter complex.

As illustrated in FIGS. 1 to 4, several synergistic effects contribute to visualizing transgene expression in vivo. First, taking as an example an engineered transferrin receptor (ETR) as the internalizing receptor and a transferrin-MION reporter complex (Tf-MION), overexpression of the ETR (ETR+) results in an approximately 5 fold higher cellular internalization of the Tf-MION per hour when compared to matched cells lacking the receptor (ETR−) (see the graph in FIG. 1). Secondly, as shown schematically in FIG. 2, during each ETR mediated internalization event, several thousand iron atoms (one MION contains an average of 2064 Fe per 3 nm particle core rather than 2 iron atoms in holo-Tf) accumulate in the cell. See also, Moore et al., *Biochimica Biophysica Acta,* 1402:239–249 (Apr. 24, 1998), incorporated herein by reference in its entirety, which discusses various experiments using this system and the new methods in vitro.

Third, upon cellular internalization and compaction in the endosome, the R2 and R2* relaxivities of the superparamagnetic MION further increases approximately 4 fold due to compartmentalization, which brings individual MIONs into sufficiently close proximity that together they achieve a synergistic increase in their individual relaxivities, causing T2 to decrease and create high local susceptibility gradients detectable by gradient echo MR pulse sequences.

Finally, cellular internalization of iron particles in the reporter complex does not down-regulate the level of ETR expression, which normally occurs when native, non-engineered transferrin receptors are exposed to increased concentrations of iron within the cell.

Figure 4:
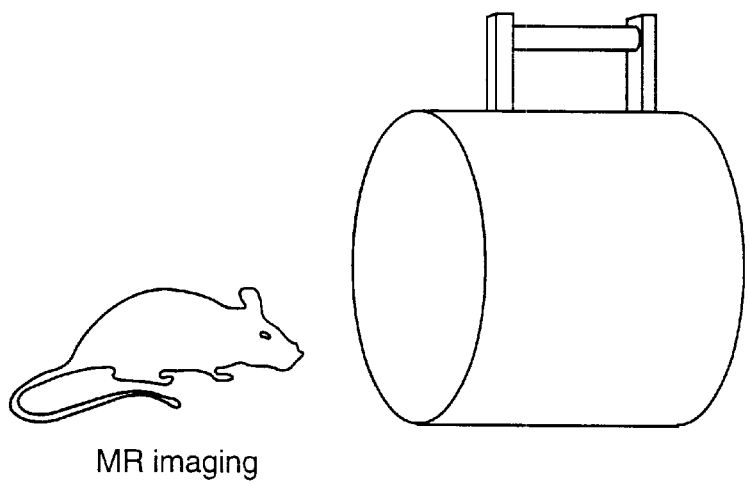
FIG. 4 is a schematic diagram of a mouse containing cells that express an internalizing receptor and, as a result, contain reporter complexes that can be imaged in vivo using MR imaging.

Compared to cellular Fe internalization through the Tf/hTfR system, the Tf-MION/ETR system results in an approximately $10^4$—fold amplification, dramatically increasing the ability to detect the cells expressing the receptor, and thus a desired transgene, by MR imaging, as shown schematically in FIG. 4.

Internalizing Receptors and Receptor-Specific Moieties

The internalizing receptors and their receptor-specific moieties should have the following characteristics:

1. the receptors must internalize into the cell, meaning that they are initially expressed on the cell surface, and move into the cell. The receptors can be activated to move into the cell either by binding of a ligand (e.g., by receptor-mediated endocytosis) or by internalizing without ligand binding. Either way, the receptor moves into the cell with the receptor ligand or antibody attached, thereby shuttling the ligand (and anything attached thereto) into the cell;

2. the receptor-specific moieties should be known, and their conjugation to a magnetic particle should not inhibit their binding to the receptor;

3. the receptors should be expressed at high levels on the cell surface;

4. the receptors should preferably, but not necessarily, recycle, i.e., move back to the cell surface, once they deliver their attached ligands to compartments within the cell to bind to additional receptor-specific moieties. Thus, one receptor molecule can internalize many receptor-specific moieties, which increases the amplification factor; and 5. the receptors and reporter complexes should be selected such that binding of the complex to the receptor does not significantly interfere with the physiology of the organism. However, limited perturbations of physiological response may be tolerated if the imaged disease is severe enough.

Various examples of exemplary receptors and their naturally occurring ligands are listed in Table 1.

TABLE 1

| RECEPTOR | LIGAND |
| --- | --- |
| Transferrin Receptor | transferrin |
| Bombesin Receptor | bombesin |
| Gastrin Receptor | gastrin |
| LDL Receptor (low density lipoprotein) | LDL |
| EGF Receptor (epidermal growth factor) | EGF |
| TNF Receptor (tumor necrosis factor) | TNF |
| TGF Receptor (tumor growth factor) | TGF |
| Beta Adrenergic Receptors | catecholamines |
| asialoglycoprotein receptor (hepatocytes) | asialofetuin |
| Somatostatin Receptor | somatostatin |
| N-formyl peptide Receptor peptides | N-formyl |
| Insulin Receptor | insulin |
| Angiotensin II Receptor | angiotensin |
| Urokinase Receptor | urokinase |
| Muscarinic Receptors | carbachol |
| Folate Receptor | folate |
| Insulin-like Growth Factor (IGF) Receptor | IGF |

Additional internalizing receptors not named in Table 1 can be used as long as they meet the criteria described herein. For example, receptors with internalizing motifs can be used. Table 2 shows a number of receptors and their internalizing signal sequences or "motifs." In Table 2, the single-letter amino acid code is used, residues in the internalization sequences critical to internalization are shown in bold type, and the following abbreviations are used: LDL, low-density lipoprotein; TfR, transferrin receptor; VIP36, vesicle integral protein 36; VAMP-2, vesicle-associated membrane protein-2. All of these sequences are referenced in Kirchhausen, Current Opinion in Cell Biology, 9:488–495 (1997), except TfR, which is referenced in Collawn et al., *Cell,* 63:1061–1072 (1990).

TABLE 2

Different classes of internalization signals

| Signal Sequence | Internalization Sequence | Receptor Protein | Reference |
|---|---|---|---|
| Tyrosine-based (NPXY-type) | FDNPVY (SEQ ID NO:1) | LDL receptor | Kirchhausen |
| Tyrosine-based (YXXØ-type) | YTRF (SEQ ID NO:2) | TfR | Collawn |
| Dileucine-based | DKQTLL (SEQ ID NO:3) | CD-3gamma | Kirchhausen |
| Acidic Clusters | WQEECPSDSEEDEGRGR (SEQ ID NO:4) | Furin | Kirchhausen |
| Dilysine (KKFF-type) | KRFY (SEQ ID NO:5) | VIP36 | Kirchhausen |
| Synaptic vesicle targeting | EVVDIMRVNV (SEQ ID NO:6) | VAMP-2 | Kirchhausen |

Other receptors that include these internalizing motifs can also be used in the methods described herein. In Table 2, the symbol Ø represents bulky amino acids, such as F, and X represents any amino acid.

For each internalizing receptor, there are one or more preferred ligands that specifically bind to the receptor. In addition, antibodies that bind to the internalizing receptor can be used as the receptor-specific moiety, and can be prepared using standard techniques. For example, when ETR is used, the preferred ligand is transferrin, or a variant or analog of transferrin, or an antibody that specifically binds to the ETR. Again, such antibodies can be made using standard techniques. Thus, receptor-specific moieties can be ligands or antibodies, or other molecules, such as small molecules (e.g., peptidomimetics) or peptides, which bind specifically to a particular internalizing receptor. Such small molecules and peptides can be molecularly engineered to inhibit their degradation by enzymes in the body to increase their biological half-life in plasma. For example, peptides can be protected against enzymatic degradation by using D-amino acids in their preparation, by substitution of their peptide bonds, by replacing disulfide bonds with thioether linkages, and by inserting unusual amino acids. The receptor-specific moieties should bind with sufficient affinity to the receptor to provide a signal that can be distinguished from any signal generated by non-specific binding. In some embodiments, for a receptor-specific moiety to be useful, it should have a high receptor binding affinity with an IC50 value in the nanomolar range. In addition, the specificity should be sufficient to avoid binding of the moiety to any non-target receptors.

Examples of receptor-specific peptides and small molecules include chemotactic peptides, somatostatin or somatostatin analogs (such as those prepared using D-amino acids, e.g., octreotide (Sandostatin® SMS 201-995), P587, and P829), bombesin analogs.

Once a receptor is chosen, the receptor can be genetically manipulated to increase its utility for imaging. For example, mutagenesis of the ETR or other native or engineered receptors has the potential to dramatically increase signal amplification resulting in substantially more sensitive and earlier detection of transgene expression. Even a modest two-fold increase in internalization can substantially reduce the detection threshold of gene expression by MR imaging. Sensitivity of this sort would allow for earlier assessment of effective gene therapy. The specific aims are as follows:

A. Mutate a native internalizing receptor (e.g., TfR) sequence or an engineered internalizing receptor (e.g., ETR) sequence to include amino acid changes known to alter TfR internalization rates and cellular accumulation of Tf. Mutatagenesis will generate a panel of singly mutated receptors, e.g., ETRs (mutETRs);

B. Determine the biological properties (receptor binding of Tf-MION, receptor internalization rate, and total Tf-MION accumulation) of the mutated internalizing receptors;

C. Determine the effect of mutant receptors on MR signal intensity using MR phantoms;

D. Combine mutations from different favorable mutated receptor candidates identified above; and E. Determine the cumulative effect of multiple mutations on biological properties of the receptor and MR signal intensity.

As illustrated in Table 2, there are various known internalization sequences, and some of these sequences have been examined to determine the critical amino acids in these sequences or motifs. For example, identification of specific amino acid sequences in the cytoplasmic tails of membrane proteins that are internalized via clathrin-coated pits has yielded consensus "internalization motifs" (Trowbridge et al., (1993) *Annu. Rev. Cell Biol.,* 9, 129–61 and Collawn et al., (1990) *Cell,* 63(5), 1061–723,4). In another example, tyrosine based motifs have been discovered (see Table 2) in which a minimum four-amino-acid-sequence containing a tyrosine at the first position of a beta-turn and a bulky hydrophobic residue at the forth position are required. The beta-tum internalization motifs are utilized in many different proteins and may share common 3-D structure (see, e.g., Bansal et al., (1991), *Cell* 67(6), 1195–201 and Eberle et al., (1991), *Cell,* 67(6), 1203–9). In addition, it has been demonstrated that the activity of the motif is independent of polarity with respect to the plasma membrane and does not have a strict requirement for proximity to the plasma membrane (Jing et al., (1990), *J. Cell. Biol.,* 110(2), 283–94; Jadot et al., (1992), *J. Biol. Chem.,* 267(16), 11069–77; and Collawn et al., (1991), *Embo. J.,* 10(11), 3247–53).

Most often this activity has been demonstrated by site-directed mutagenesis to alter the motif resulting in lower internalization rates. In the case of the TfR a tetrapeptide YTRF (see Table 2), between amino acids 20–23 of the cytoplasmic domain, has been identified as the minimum sequence required for internalization (Colawn et al. 1990). Further, Pytowski et al., (*J. Biol. Chem.,* 270(16), 9067–73, 1995) have demonstrated that mutation of glycine at position 31 or serine 34 in the cytoplasmic tail of the TfR to a tyrosine restores wild-type levels of internalization to mutant TfR lacking a consensus internalization motif. These data suggest that substituting a tyrosine at the first or last position of the tetrapeptide GDNS (residues 31–34) can create an internalization motif This motif is predicted to form a tight turn within the cytoplasmic domain of the hTfR. In addition, these results indicate that substitution of tyrosine at position 31 or at position 34 in a TfR containing an unaltered wild-type internalization motif increases the level of receptor internalization almost 2-fold. For cells expressing the gly31tyr change this resulted in approximately a 5-fold increase in cell associated 55Fe in six hours compared to cells expressing wild type TfR (Pytowski et al., 1995).

Other studies have investigated palmitoylation sites. For example, the human TfR can be post-translationally modified by the covalent attachment of palmitic acid to Cys62 and Cys67 via a thio-ester bond, When TfR receptors mutated to express an alanine or a serine at both positions 62 and 67 are expressed in CHO cells there is significant increase in receptor internalization resulting in an increased rate of [59Fe] diferric Tf accumulation. No effect on the rate of receptor recycling was detectable. Alvarez et al. (*J. Biol. Chem.*, 265(27), 16644–55, 1990) have shown that substituting a serine at both position 62 and 67 results in approximately a 2-fold increase in the apparent first order rate constant for TfR endocytosis and a 2.6-fold increase in diferric transferrin uptake. Substitution of alanine for cysteine at both these positions resulted in more modest effects on the apparent rate constant and diferric transferrin uptake (approx. 1.5-fold and 2-fold, respectively).

Figure 3:
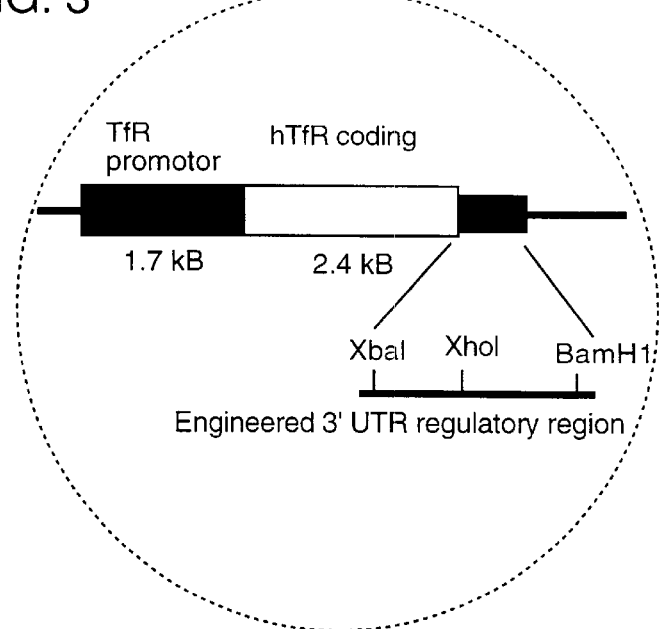
FIG. 3 is a schematic representation of an engineered, altered expression human transferrin receptor (ETR) encoding expression cassette that is inserted into cells to induce them to express the altered ETR.

One example of a specific internalizing receptor is a human transferrin receptor that is engineered to lack the mRNA destabilization motifs in the 3' UTR and therefore constitutively over-expresses high levels of the receptor protein in the cell (FIG. 3). This is reflected in a substantial (5-fold) increase in holo-TR bound by stably-transfected cells in culture (see FIG. 1). This receptor is referred to herein as an engineered transferrin receptor or ETR.

As shown schematically in FIG. 3, the ETR cDNA sequence consists of the hTfR promoter (1.7 kB), the coding sequence (2.4 kB), and the engineered 3'UTR regulatory sequence, which includes several known restriction sites.

The expression construct for the ETR cDNA sequence, e.g., a plasmid, contains the endogenous human transferrin receptor promoter driving expression of a human transferrin receptor cDNA. A plasmid in which the cDNA is modified to include the complete coding region of the TfR with truncated 5'-and 3'-UTR is described in Casey et al., *EMBO J.*, 8:3693–3699 (1989) and Casey et al., *PNAS, USA*, 85:11787–1791 (1988). In addition, deletions of the truncated 3'-UTR were made to remove the iron regulatory sequences and endogenous mRNA instability sequences. Since the transferrin receptor expression is controlled by the iron-dependent regulation of TfR mRNA levels, these deletions render a constitutively expressed receptor whose expression is no longer under the control of the iron level in the cell.

The nucleic acid encoding the internalizing receptor can be combined with a desired transgene, in the same or a new vector, and preferably under the control of the same promoter or expression enhancers, to yield a gene delivery vector in which the desired gene is expressed at a constant ratio with the internalizing receptor. In this way detection of a reporter complex by MRI indicates transgene expression. This can be achieved in several ways.

First, the internalizing receptor and transgene can be expressed as a bicistronic nucleic acid construct, which includes an mRNA transcribed from a single promotor where expression of the gene in the second coding region is directed by an internal ribosome entry site (IRES). Either gene can be in position 1, with the other gene in position 2. The positional effect is determined empirically before clinical imaging.

Second, the two genes can be expressed on the same plasmid or nucleic acid construct (amplicon) under the control of two different copies of the same promoter or two different promoters. The use of different promoters is determined empirically and is related to the level of transfer expression necessary to get a therapeutic effect and the level of internalizing receptor to get a useful MR imaging signal. The order of gene arrangement is not restricted (i.e., either gene can be "first"), but again is tested empirically before the construct is used for clinical imaging.

Third, each gene can be expressed by separate nucleic acid constructs, both administered simultaneously. The promoters can be the same or different.

Gene delivery vehicles or vectors that contain a nucleic acid construct including a desired gene and a sequence encoding an internalizing receptor such as ETR as a reporter can be constructed using standard techniques. DNA is typically delivered into target cells by one of three methods: 1) enclosing it in a virus ("viral vector"), 2) attaching it to a synthetic delivery system ("artificial vector"), or 3) by mechanical means, e.g., by electroporation or using gold particle bombardment, i.e., with a "gene gun." Current gene technology has focused primarily on the use of viral vectors which provide highly efficient transduction and high levels of gene expression, as several viruses have efficient mechanisms for transferring genetic material into target cells. The precise design of a particular viral vector depends largely on the type of virus used and the type of effect be achieved.

In the case of increased internalizing receptor expression, e.g., on a rapidly proliferating cancer cell, these cells (and thus the solid tumors) can be imaged without the need for any vectors, simply by administering to the animal or human subject an effective amount of a reporter complex with a receptor-specific moiety.

Other delivery vehicles include retroviruses, which are used in most clinical trials of ex vivo gene transfer, and which are RNA viruses that replicate through a DNA intermediate synthesized by reverse transcriptase. These viruses enter the cell by direct fusion to the cellular membrane and then integrate in stable form into the host chromosome during cell division. Such retroviruses may be preferred in certain long-term therapies, whereas the constructs and amplicons described herein are useful for short-term therapy, e.g., for tumor therapy.

Adenoviruses can also be used. These viruses contain double-stranded DNA and enter the cell by receptor-mediated endocytosis, but their genomes do not integrate into the host and therefore have no oncogenic potential. Adenoviruses are widely used in gene transfer because they are easy to construct and are generally not perceived as toxic to cells.

Herpes simplex virus (HSV) can also be used as a vector. HSV is a large double-stranded DNA virus that enters cells by direct fusion. HSV vectors are useful for gene transfer to tumors because of several features including: 1) ability to carry up to 250 kB of transgenes; 2) stable expression of transgene sequences even in replicating cells, due to the extrachromosomal nature of the amplicon; 3) high efficiency at low multiplicity of infection (MOI); 4) infectivity of most human and primate cell lines; 5) a high efficiency in tumor cells; and 6) relatively low immunogenicity. Thus, HSV derived amplicons provide a useful method of gene delivery.

Amplicons are plasmids that can be packaged to high titers and used to transfer anticancer genes in vitro and in vivo, although the vector itself does not possess oncolytic functions. Amplicons can be packaged as multiple copies into each viral particle (about 10 copies of pHEA1) making their use an efficient method of plasmid delivery. Another advantage of amplicons is that they are maintained extrachromosomally in replicating cells because of the EBNA1 signal assuring passage to dividing daughter tumor cells. Finally, amplicons, like adenoviruses, show little toxicity.

Figure 5:
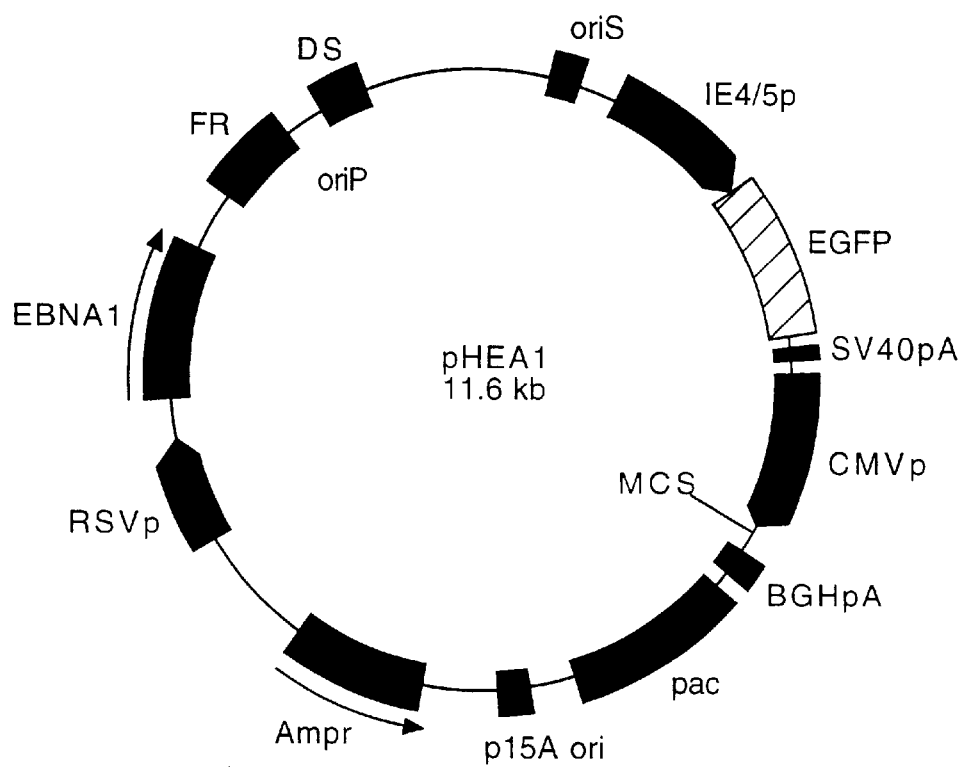
FIG. 5 is a schematic representation of an HSV/EBV hybrid amplicon (pHEA1).

To achieve high and stable levels of transgene expression in vivo, a hybrid HSV/EBV amplicon can be engineered as described, e.g., in Wang et al., *J. Virology*, 70:8422–30 (1996). For example, an HSV/EBV amplicon was constructed and successfully used to obtain stable levels of expression of reporter transgenes, such as luciferase and green fluorescence protein (GFP), in vitro and in vivo. As shown in FIG. 5, this HSV/EBV hybrid amplicon (PHEA1) consists of a plasmid containing the following elements: (1) the herpes simplex origin of DNA replication (oriS) and packaging signal (pac) to allow for packaging of the plasmid amplicon into HSV capsid/envelopes, after co-transfection with a set of five cosmids that overlap and represent the entire HSV-1 genome but which were mutated to inactivate the pac signals; (2) the EBNA-1 gene and ori-p of the Epstein-Barr virus (EBV) to allow for autonomous replication and nuclear retention of the amplicon in infected cells, thereby allowing for the amplicon's permanence within the nucleus of infected cells; (3) a multiple cloning site (MCS) preceded by the cytomegalovirus (CMV) promoter driving the expression of a polycistronic element consisting of marker genes linked by an internal ribosome entry site (IRES); and (4) enhanced GFP (EGFP) driven by the HSV IE4/5p promoter for easy determination of vector titers. In this construct, the EGFP represents the desired transgene.

Figure 6:
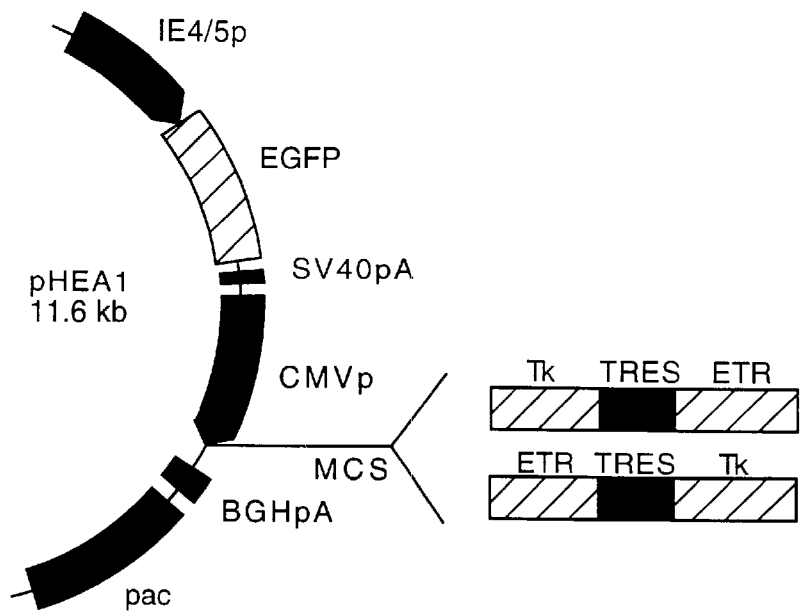
FIG. 6 is a schematic representation of a portion of the HSV/EBV hybrid amplicon of FIG. 5, showing the multiple cloning site (MCS) and two nucleic acid inserts encoding the engineered transferrin receptor, an internal ribosome entry site (IRES), and a desired gene, thymidine kinase (Tk), in two different orientations.

Because the location of ETR in the polycistronic element may affect gene expression, different inserts, such as Tk-IRES-ETR and ETR-IRES-Tk, can be tested. As shown in FIG. 6, these two nucleic acid constructs merely alter the order of the ETR and desired gene (thymidine kinase, Tk). In each case, the gene constructs are inserted into the multiple cloning site (MCS) of the amplicon.

Control vectors are "empty" amplicons without inserts. The amplicons are packaged by co-transfection with a set of cosmids without pac signal into 2-2 cells. After harvesting viral supernatants, they are concentrated by sucrose gradient centrifugation to achieve titers of $1\times10^8$ to $1\times10^9$ TU/mL. Additional rounds of centrifugation can be performed to achieve higher titers.

Expression of the transgenes can be tested by infecting human U87δEGFR or Gli36EGFR cells and assaying for EGFR expression to determine the titers of vector stock. Proliferative abilities of the cells after infection with the amplicon can be assayed by comparing the proliferation of the uninfected U87δEGFR or Gli36EGFR cells with cells infected with either HSV/EBV hybrid amplicon and/or mock-infected cells. Stability of transgene expression can be determined by assaying ETR expression over time.

Other viral or non-viral gene delivery systems including the nucleic acid constructs described herein along with any desired gene, e.g., a therapeutic gene, can be prepared using standard techniques.

Reporter Complexes

The reporter complexes are prepared by conjugating or linking one or more receptor-specific moieties, such as ligands, antibodies, small molecules or peptides, to one or more reporter groups such as magnetic particles that change the relaxivity of the cells once internalized so that they can be imaged using MRI. The receptor-specific moieties can be linked to the magnetic particles by a variety of methods, including, e.g., bifunctional chemical linkers or spacers such as SPDP, avidin-biotin coupling, charge-coupling, heat exchange, absorption, or other linkers.

The receptor-specific moieties in the reporter complex can be naturally occurring ligands, altered ligands or analogs, antibodies prepared using standard techniques to specifically bind to the receptor, or small molecules or peptides that bind specifically to the receptor. The use of small molecules or peptides can avoid competition with the natural ligand if these molecules do not bind to the main active site of the receptor, and can also avoid inducing a physiological response by the receptor, which may be beneficial. Of course, the small molecules or peptides should not interfere with the receptors internalization.

The magnetic particles in the reporter complex can be superparamagnetic, ferromagnetic, or paramagnetic, and can range in size from about 1 to about 200 nanometers or larger, e.g., 300 or 350 mn, as long as they can still be internalized by the cells. Thus, the magnetic particles are typically nanoparticles.

Specific examples of such magnetic nanoparticles include monocrystalline iron oxide nanoparticles (MIONs) as described in various U.S. patents and journal articles, e.g., in U.S. Pat. No. 5,492,814; Whitehead, U.S. Pat. No. 4,554, 088; Molday, U.S. Pat. No. 4,452,773; Graman, U.S. Pat. No. 4,827,945; and Toselson et al., Bioconj. Chemistry, 10:186–191 (1999). The particles can also be superparamagnetic iron oxide particles (SPIOs), ultra small superparamagnetic iron oxide particles (USPIOs), and cross-linked iron oxide (CLIO) particles (see, e.g., U.S. Pat. No. 5,262, 176).

MIONs consist of a central 3 nm monocrystalline magnetite-like single crystal core to which are attached an average of 12 10 kD dextran molecules resulting in an overall size of 20 nm (as described in U.S. Pat. No. 5,492, 814 and in Shen et al., "Monocrystalline iron oxide nanocompounds (MION): physicochemical properties," Magnetic Resonance in Medicine, 29:599–604 (1993), to which proteins and peptides can be conjugated for targeted delivery, e.g., as described in Shen et al., Bioconjugate Chemistry, 7:311–316 (1996). See also, Weissleder et al., Nature Medicine, 6(3):351–354 (March 2000). The dextran/Fe w/w ratio of a MION is 1.6:1. R1=12.5 mM sec-1, R2=45.1 mM sec-1 (0.47T, 38° C.). MIONs elute as a single narrow peak by high performance liquid chromatography with a dispersion index of 1.034; the median MION particle diameter corresponds in size to a protein with a mass of 775 kD and contains an average of 2064 iron molecules.

One example of a reporter complex comprises a transferrin molecule, such as human holo-transferrin (Tf), which is a form of transferrin that contains two iron atoms, covalently conjugated (or charge coupled) to a MION. The use of transferrin as the receptor-specific moiety typically provides lower immunogenicity than an anti-transferrin receptor antibody, but both can be used as the receptor-specific moiety, as long as the antibodies do not interfere with receptor internalization.

The physicochemical and biological properties of the magnetic particles can be improved by crosslinking the dextran coating of magnetic nanoparticles to form CLIOs to increase blood half-life and stability of the reporter complex. The cross-linked dextran coating cages the iron oxide crystal, minimizing opsonization. Furthermore, this technology allows for slightly larger iron cores during initial synthesis, which improves the R2 relaxivity.

Another example of a reporter complex comprises holo-transferrin and CLIOs. CLIOs were synthesized by crosslinking the dextran coating of generic iron oxide particles (e.g., as described in U.S. Pat. No. 4,492,814) with epibromohydrin to yield CLIOs as described an U.S. Pat. No. 5,262,176. CLIOs were reacted with periodate at different ratios (0.1–5 mg $NaIO_4$/1 mg Fe) and dialyzed against sodium bicarbonate buffer (0.02 M sodium bicarbonate, 0.15 M sodium chloride, pH 8.7. The partially oxidized CLIOs were reacted with human holo-Tf ($^{125}$I 2.35 μCi/mg labeled) to result in Tf-CLIOs with the following approximate CLIO/Tf ratios: 1:1, 1:3, 1:5, 1:7. Sodium cyanoborohydrate was then added at 1 mg/ml and conjugates left overnight at 4° C. Conjugates were purified on a BioGel 1.5A column (Bio-Rad, Richmond, Calif.).

The physicochemical and biological properties of different (Tf)n-CLIO complexes or conjugates (such as size, magnetic properties, lyophilization, stability blood half-life) can be altered by varying aldehyde generation to yield different Tf/CLIO ratios.

The yield of attachment of Tf to CLIO can be determined with a protein determination kit based on bicinchoninic acid (562 nm, Pierce); iron is determined spectrophotometrically. The size of particles can be measured using a Coulter N-4 particle size analyzer.

The relaxivities of the different constructs are calculated as the slopes of the curves of 1/T1 and 1/T2 vs. iron concentration; T1 and T2 relaxation times are determined using a Bruker NMS-120 Minispec MR spectrometer (Bruker Instruments, Canada) operating at a 0.47 T (20 MHz) and 37° C. Stability of the conjugates can be tested by treating them under different storage conditions (4° C., 21° C. and 37° C. for different periods of time) and performing HPLC analysis of aliquots as well as binding studies using stably transfected 9L cells expressing the ETR (as described herein).

Methods of Imaging

MR imaging can be performed in live animals or human patients using standard MR imaging equipment, e.g., having a 1.5 T superconducting magnet. Imaging protocols typically consist of $T_1$, $T_2$, and $T_2^*$ diffusion weighted and other MR pulse sequences, coronal T1 weighted spin echo (SE 300/12), T2 weighted SE (SE 3000/variable TE) and gradient echo (GE 50/variable TE/variable flip angle) sequences at different time points before and after intravenous administration of a reporter complex, such as Tf-MION (10 mg Fe/kg).

To determine the in vivo distribution of a particular reporter complex, biodistribution studies and nuclear imaging can be carried out using excised tumors of animals that have received a single dose of labeled reporter complex, e.g., Tf-MION (30 $\mu$Ci/animal). In the case of Tf-MION, 24 hours after IV administration of the reporter complex, mean accumulation in ETR+ tumors was 3.2% ID/g tumor while it was significantly lower in ETR− tumors in the same animal (0.8% ID/g; p<0.001). A similar 4-fold difference was also observed when In labeled Tf was injected into these animals. The same assay can be used to analyze the biodistribution of other new reporter complexes.

To determine whether expression of a specific transgene can be revealed with a particular reporter complex, animals receive an IV injection of the complex. After injection, differences in MR signal-to-noise ratios are determined. If significant, the reporter complex can be used in clinical imaging of that specific transgene. Biodistribution studies can be used to show a higher concentration of the reporter complex in cells expressing the internalizing receptor compared to matched cells that do not express (or overexpress) the internalizing receptor in the same animal.

Transgenic Animals

The nucleic acid constructs described herein can also be used to prepare transgenic animals, which are non-human animals (e.g., a mammal such as a non-human primate, dog, cat, cow, pig, goat, sheep, horse, rabbit, mouse, rat, guinea pig, or hamster) in which one or more of the cells of the animal includes a transgene. A "transgene" is any exogenous nucleic acid sequence that is integrated into the genome of a cell from which a transgenic animal develops and which remains in the genome of the mature animal. Such animals can be mosaics or have the desired genes in all cells. The nucleic acid constructs of the transgene can include a "regulatory sequence," which is a DNA sequence that directs the transcription of a gene in a cell. Expression control or regulatory sequences are "operably linked" to a nucleic acid when they are positioned to effectively control expression of the nucleic acid. Typically, the expression control or regulatory sequences are located upstream of the nucleic acid in terms of the direction of transcription.

The transgene includes a nucleic acid sequence that encodes an internalizing receptor operably linked to a regulatory sequence, which is introduced into both the somatic and germ cells, or only some of the somatic cells of an animal. The transgene is introduced in such a manner that the inserted transgene can be expressed and produced in the animal. The regulatory sequence drives expression of the receptor gene. The term regulatory sequence includes promoters, enhancers, and other expression control elements. It will be appreciated that the appropriate regulatory sequence depends on such factors as the future use of the transgenic animal, and the level of expression of the receptor polypeptide desired. A person skilled in the art would be able to choose the appropriate regulatory sequence.

Examples of various regulatory sequences are described below; they can be inducible or constitutive. Suitable constitutive regulatory sequences include the regulatory sequence of a housekeeping gene such as the α-actin regulatory sequence, or may be of viral origin such as regulatory sequences derived from mouse mammary tumor virus (MMTV) or cytomegalovirus (CMV).

Alternatively, the regulatory sequence can direct transgene expression in specific organs or cell types. Several tissue-specific regulatory sequences are known in the art including the albumin regulatory sequence for liver (Pinkert et al., 1987, Genes Dev. 1:268–276); the endothelin regulatory sequence for endothelial cells (Lee, 1990, J. Biol. Chem., 265:10446–50); the keratin regulatory sequence for epidermis; the myosin light chain-2 regulatory sequence for heart (Lee et al., 1992, J. Biol. Chem., 267:15875–85), and the insulin regulatory sequence for pancreas (Bucchini et al., 1986, Proc. Natl. Acad. Sci., 83:2511–2515.

In addition, expression of the transgene can be precisely regulated, for example, an inducible regulatory sequence such as a regulatory sequence that is sensitive to certain physiological regulators, e.g., circulating glucose levels, or hormones (Docherty et al., 1994 FASEB J., 8:20–24) can be used.

A number of methods have been used to obtain transgenic, non-human animals, which are animals that have gained an additional gene by the introduction of a transgene into their cells (e.g., both the somatic and germ cells), or into an ancestor's germ line.

Methods for generating transgenic animals include introducing the transgene into the germ line of the animal. One method is by microinjection of a gene construct into the pronucleus of an early stage embryo (e.g., before the four-cell stage; Wagner et al., 1981, Proc. Natl. Acad. Sci., USA, 78:5016; Brinster et al., 1985, Proc. Natl. Acad. Sci., USA, 82:4438). Alternatively, the transgene can be introduced into the pronucleus by retroviral infection. A detailed procedure for producing such transgenic mice has been described (see e.g., Hogan et al., Manipulating the Mouse Embryo, Cold Spring Harbour Laboratory, Cold Spring Harbour, N.Y. (1986); U.S. Pat. No. 5,175,383 (1992)). This procedure has also been adapted for other animal species (e.g., Hammer et al., Nature 315:680 (1985); Murray et al., Reprod. Fert. Devl. 1:147 (1989); Pursel et al., Vet. Immunol. Histopath. 17:303 (1987); Rexroad et al., J. Reprod. Fert. 41 (suppl): 119 (1990); Rexroad et al., Molec. Reprod. Devl. 1:164 (1989); Simons et al., BioTechnology 6:179 (1988); Vize et al., J. Cell. Sci. 90:295 (1988); and Wagner, J. Cell. Biochem. 13B (suppl):164 (1989)). In brief, the procedure involves introducing the transgene into an animal by microinjecting the construct into the pronuclei of the fertilized mammalian egg(s) to cause one or more copies of the transgene to be retained in the cells of the developing mammal(s). Following introduction of the transgene construct into the fertilized egg, the egg may be incubated in vitro for varying amounts of time, or reimplanted into a surrogate host, or both. One common method is to incubate the embryos in vitro for about 1–7 days, depending on the species, and then reimplant them into the surrogate host. The presence of the transgene in the progeny of the transgenically manipulated embryos can be tested by Southern blot analysis of a segment of tissue.

Another method for producing germ-line transgenic animals is through the use of embryonic stem (ES) cells. The gene construct can be introduced into embryonic stem cells by homologous recombination (Thomas et al., Cell, 51:503 (1987); Capecchi, Science, 244:1288 (1989); Joyner et al., Nature, 338:153 (1989)) in a transcriptionally active region of the genome. A suitable construct can also be introduced into embryonic stem cells by DNA-mediated transfection, such as by electroporation (Ausubel et al., Current Protocols in Molecular Biology, John Wiley & Sons (1987)). Detailed procedures for culturing embryonic stem cells (e.g., ES-D3, ATCC# CCL-1934, ES-E14TG2a, ATCC# CCL-1821, American Type Culture Collection, Rockville, Md.) and methods of making transgenic animals from embryonic stem cells can be found in Teratocarcinomas and Embryonic Stem Cells, A Practical Approach, ed. E. J. Robertson (IRL Press, 1987). In brief, the ES cells are obtained from pre-implantation embryos cultured in vitro (Evans, M. J., et al., 1981, Nature, 292:154–156). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal.

In the above methods, the transgenic construct can be introduced as a linear construct, a circular plasmid, or a viral vector, which can be incorporated and inherited as a transgene integrated into the host genome. The transgene can also be constructed so as to permit it to be inherited as an extrachromosomal plasmid (Gassmann, M. et al., 1995, Proc. Natl. Acad. Sci. USA 92:1292). A plasmid is a DNA molecule that can replicate autonomously in a host.

The transgenic, non-human animals can also be obtained by infecting new cells either in vivo (e.g., direct injection), ex vivo (e.g., infecting the cells outside the host and later reimplanting), or in vitro (e.g., infecting the cells outside host) with a recombinant viral vector carrying the internalizing receptor gene. Examples of suitable viral vectors include recombinant retroviral vectors (Valerio et al., 1989, Gene, 84:419; Scharfinan et al., 1991, Proc. Natl. Acad. Sci., USA, 88:462; Miller, D.G. & Buttimore, C., 1986, Mol. Cell. Biol., 6:2895), recombinant adenoviral vectors (Freidman et al., 1986, Mol. Cell. Biol., 6:3791; Levrero et al., 1991, Gene, 101:195), and recombinant Herpes simplex viral vectors (Fink et al., 1992, Human Gene Therapy, 3:11). Recombinant retroviral vectors capable of transducing and expressing structural genes inserted into the genome of a cell are produced by transfecting the recombinant retroviral genome into suitable packaging cell lines such as PA317 and Psi-CRIP (Cornette et al., 1991, Human Gene Therapy 2:5–10; Cone et al., 1984, Proc. Natl. Acad. Sci., USA, 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the distinct advantage of not requiring mitotically active cells for infection.

Clones of the non-human transgenic animals described herein can be produced according to the methods described in Wilmut et al. ((1997) Nature, 385:810–813) and PCT publication Nos. WO 97/07668 and WO 97/07669. In brief, a cell, e.g., a somatic cell from the transgenic animal, can be isolated and induced to exit the growth cycle and enter the $G_o$ phase to become quiescent. The quiescent cell can then be fused, e.g., through the use of electrical pulses, to an enucleated oocyte from an animal of the same species from which the quiescent cell is isolated. The reconstructed oocyte is then cultured such that it develops into a morula or blastocyte and is then transferred to a pseudopregnant female foster animal. Offspring borne of this female foster animal will be clones of the animal from which the cell, e.g., the somatic cell, was isolated.

Once the transgenic animal is produced, cells of the transgenic animal and cells from a control animal are screened to determine for the presence of a nucleic acid sequence encoding an internalizing receptor, e.g., using polymerase chain reaction (PCR). Alternatively, the cells can be screened to determine if the desired mRNA is expressed (e.g., mRNA can be detected by standard procedures such as Northern blot analysis or reverse transcriptase-polymerase chain reaction (RT-PCR); Sambrook et al., Molecular Cloning—A Laboratory Manual, (Cold Spring Harbor Laboratory, 1989)) or if receptor protein is produced (e.g., receptor proteins can be detected using Western blot analysis; Sambrook et al., Molecular Cloning—A Laboratory Manual, (Cold Spring Harbor Laboratory, 1989)).

These transgenic animals can be used, for example, to study the developmental regulation of promoters. An appropriate reporter complex is administered to the animal, and the animal is imaged to determine the temporal expression of the internalizing receptor, as well as the anatomical localization of expression of the receptor where non-tissue-specific promoters are used.

Uses

The new methods and compositions have numerous practical applications. The availability of a universal MR marker gene (the nucleic acid constructs encoding the internalizing receptors) to image gene expression is important for monitoring gene therapy where exogenous genes are introduced to ameliorate a genetic defect or to add an additional gene function to cells.

The new methods can also used to image endogenous gene expression during development and/or pathogenesis of disease. As described above, with advances in establishing transgenic mouse models, the new compositions can be used to develop an animal line that has an imaging marker (internalizing receptor) gene under the control of a given promoter under study, so that promoter activity can be directly visualized. Preliminary studies using green fluorescent protein (GFP) as an imaging marker gene have already shown the feasibility of imaging VEGF promoter activity in inflammation and tumorigenesis, and similar approaches have been taken with luciferase.

The new methods can also be used for imaging gene expression in deep organs using MR imaging, and for imaging tumors that overexpress internalizing receptors compared to normal cells.

Moreover, imaging of gene expression by high-resolution MR imaging will have a major impact in the treatment of CNS disease such as brain tumors or neurodegenerative diseases. First, the magnetic imaging marker gene could be used for in vivo monitoring of gene expression analogous to marker genes used in biopsy samples (e.g., lacZ or GFP). This will have direct applications in determining efficacy and persistence of gene therapy by non-invasive imaging and imaging gene expression over time in the same subject.

By combining previously developed techniques for tracking virions or other gene delivery vehicles with gene expression imaging, one would also be able to directly compare gene delivery and gene expression in vivo. This provides a powerful tool to study the mechanism by which viral and non-viral vectors accumulate in and transduce/transfect tumors.

The new methods will also be useful in testing many of the anticipated new vectors that are currently being designed in an effort of creating safer and more efficient gene delivery systems. In addition, there are a number of strategies in place to improve viral gene delivery to brain tumors, either by modifying the blood-brain-barrier (BBB) or by targeting viruses. Irrespective of the strategy, methods that can quantitate delivery and follow gene expression over time are necessary tools in the development of gene therapy.

In addition to imaging gene transfer, the new internalizing receptor genes can be inserted into stem cells or embryonal cells to yield "magnetically marked cell lines" that can be tracked non-invasively over time. This would have useful applications for imaging studies in developmental biology, which is currently limited to anatomic structures.

EXAMPLES

The invention is further described in the following examples, which do not limit the scope of the invention described in the claims.

Example 1
Plasmids Encoding ETR

The construction of plasmids containing the cDNA for ETR (TRS-3) has been described in Casey et al. 1988 and Casey et al. 1989 (supra). The G418 resistance expression plasmid contains a neomycin phosphotransferase cDNA under control of the Rous sarcoma virus promoter. Stable clones expressing the ETR were obtained as described in Moore et al., 1998, supra. Stable transfected cells were maintained in the absence of G418 but were periodically passaged in G418 containing medium to assure integrity of the plasmid expression.

Example 2
Tf-MION Localization in Cells

To assure that Tf-MIONs localized with ETR after cellular internalization, experiments with rhodaminated Tf-MIONs and FITC labeled antihuman TfR monoclonal antibody were conducted in stable transfected ETR+ 9L cells. These studies showed the two markers to be localized in similar appearing intracellular compartments within 30 minutes after incubation. These results support the premise that increased levels of ETR expression result in increased uptake of Tf-MION and complement data showing efficient cellular internalization of Tf-MION into ETR+ cells.

Example 3
Introducing ETR+ Cells into Mice

To demonstrate that ETR expression correlated with increases in internalized Tf-MION, nude mice were implanted with both stably transfected (ETR+) and control transfected (ETR−) 9L gliosarcoma cells. First, rat 9L gliosarcoma cells (Brain Tumor Research Center, San Francisco, Calif.) were grown in Dulbecco's modified Eagle's medium (DMEM, Cellgro, Mediatech, Washington, D.C.) containing 10% fetal bovine serum (FBS, Cellgro).

Then, ETR− and ETR+ tumors were grown in nude mice by injecting 10 cells of either cell line into the left and right flanks of animals (n=12). Each animal was implanted with both tumors in each flank so that it could serve as its own control. Animals were used for histology, MR, and/or biodistribution studies 10 to 14 days after tumor inoculation. The growth characteristics of the tumors were similar and by day 12 all animals had developed tumors 200–400 mg in size. Comparison of immunostained sections from ETR+ and ETR− tumors of the same animal revealed that only tumors derived from the ETR transfected cells overexpressed the receptor. Comparison of iron staining in the same tumors also demonstrated that ETR+ tumors had increased staining for iron compared to ETR− tumors.

ETR expression in tumors was also confirmed by RT-PCR and immunohistochemistry.

Example 4
Receptor-Specific Reporter Complexes

A reporter complex was prepared from magnetic particles and holo-transferrin. Dextran coated monocrystalline iron oxide nanoparticles (MIONS) were synthesized as described in more detail in U.S. Pat. No. 5,492,814 and Shen et al., 1993. Particles were purified by dialysis against acetate buffer (0.01 M sodium acetate, 0.15 M sodium chloride, pH 6) and stored at 4° C. for further use.

MION conjugation to holo-Tf was carried out by partial oxidation of dextran, protein binding, and subsequent reduction of Schiff's bases. MIONs were initially oxidized with sodium periodate (1 mg NaIO4/1 mg Fe) for 40 minutes in the dark, dialyzed against sodium bicarbonate buffer (0.02 M sodium bicarbonate, 0.15 M sodium chloride, pH 8.7) for 1 hour, and then against 0.15 M sodium chloride for another hour. $^{125}I$ labeled holo-Tf was added to oxidized MIONs and incubated for 3 hours at room temperature. Sodium cyanoborohydrate was then added at 1 mg/ml and conjugates were left overnight at 4° C. Conjugates were purified on a BioGel 1.5A column (Bio-Rad, Richmond, Calif.). Each particle contained an average of 2 Tf and by laser light scattering had a size of 39.6±1.3 nm.

Another reporter complex, referred to as a Tf-SPDP-CLIO imaging probe was also synthesized, as follows. As discussed below, SPDP linkage of Tf to CLIO results in a higher contrast reporter complex (imaging probe).

A clonal cell line of rat 9L glioma cells stably transfected with the TfR (9L3.9 cells) was incubated with increasing concentrations of either Tf-MION (formed by conjugating holo-Tf to MION using the periodate method described above), Tf-CLIO (formed by conjugating holo-Tf to CLIO using the periodate method described above), or Tf-SPDP-CLIO (holo-Tf conjugated to CLIO using a chemical crosslinking agent, N-succinimidyl 3-(2-pyridyldithio) propionate SPDP). Concentration labels in FIG. 7 refer to the amount of iron (reporter complex) added to the sample. The ratio of Tf conjugated to iron nanoparticles for Tf-MION was 0.6:1, for Tf-CLIO was 1.2:1, and for Tf-SPDP-CLIO was 4:1.

Figure 7:
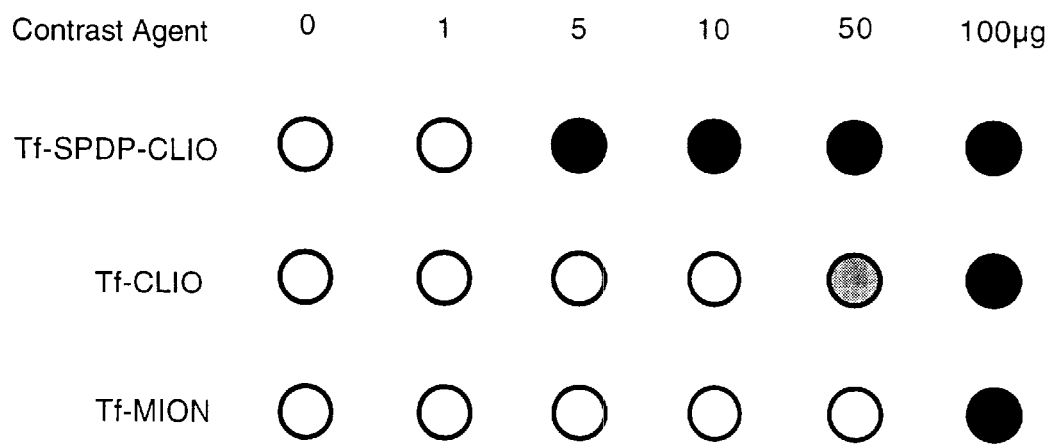
FIG. 7 is an in vitro magnetic resonance image of a top view of cell pellets in test tubes containing varying concentrations of three different contrast agents, Tf-SPDP-CLIO, Tf-CLIO, and Tf-MION.

Incubations of the reporter complexes with the cells were carried out at 37° C. The cells were washed and pelleted, and pellets were imaged in microfuge test tubes at room temperature as follows: SE (Spin Echo): TR 3000 ms, multi-echo with TE 25, 50, 75, 100 ms. Slice thickness was 1.9 mm, field of view 8 cm, matrix 256×256, 2 NEX, scan time 26:12 minutes. The resulting image of a "slice" through the cell pellets is shown in FIG. 7. As shown at the top row in the figure, the Tf-SPDP-CLIO contrast agent provided a change in measured signal at far lower concentrations of the reporter complex. Thus, this contrast agent provided a 15-fold better contrast than the first generation Tf-MION whose results are shown at the bottom of FIG. 7. The Tf-CLIO was also better than the Tf-MION, but not as good as the Tf-SPDP-CLIO.

Example 5

In vivo Imaging

To determine whether transgene expression could be revealed with the targeted nanoparticles in live animals, nude mice were implanted with both ETR+ and ETR− tumors and received an intravenous injection of the Tf/MION reporter complex. Prior to intravenous Tf-MION injection, MR imaging of animals revealed no significant differences in tumor signal intensity using either T1 or T2 weighted imaging pulse sequences. These results indicate that sources of endogenous di-ferric iron are not sufficient in altering image contrast, similar to what had been observed previously in cell culture experiments.

MR imaging was performed in live animals using a 1.5 T superconducting magnet (Signa 5.0; GE Medical Systems, Milwaukee, Wis.) using a 5-inch surface coil. The imaging protocol consisted of coronal T1 weighted spin echo (SE 300/12), T2 weighted SE (SE 3000/variable TE) and gradient echo (GE 50/variable TE/variable flip angle) sequences at different time points before and after intravenous administration of Tf-MION (10 mg Fe/kg). Slice thickness was 3 mm. The field of view (FOV) was 10 cm$^2$, using a 256×256 imaging matrix and 2–4 acquisition averages. Signal intensity (SI) measurements were obtained in regions of interest (ROI) from tumor and background. To display MION-Tf induced changes, R2 maps of tumors calculated from spin echo images were superimposed on anatomic maps (T1 weighted images). Semiquantitation was done by calibrating R2 maps to known concentrations of radiolabeled superparagmagnetic probes.

Significant differences in MR signal-to-noise ratios between ETR+ (1.7"0.2) and ETR− (9.1 "1.4) were observed (p<0.01). These differences in MR signal intensity were most pronounced using T2 and T2* weighted imaging pulse sequences consistent with the increased R2 upon cellular internalization (from 45 mMsec$^{-1}$ to 178 mMsec$^{-1}$).

The imaging data are also consistent with biodistribution studies showing a higher concentration of the reporter complex (probe) in ETR+ (3.2% ID/g) compared to matched ETR− (0.8% ID/g) tumors in the same animal. The MR signal intensity differences of tumors persisted for approximately 7 days after which tumoral signal intensity returned to baseline values.

Figure 8:
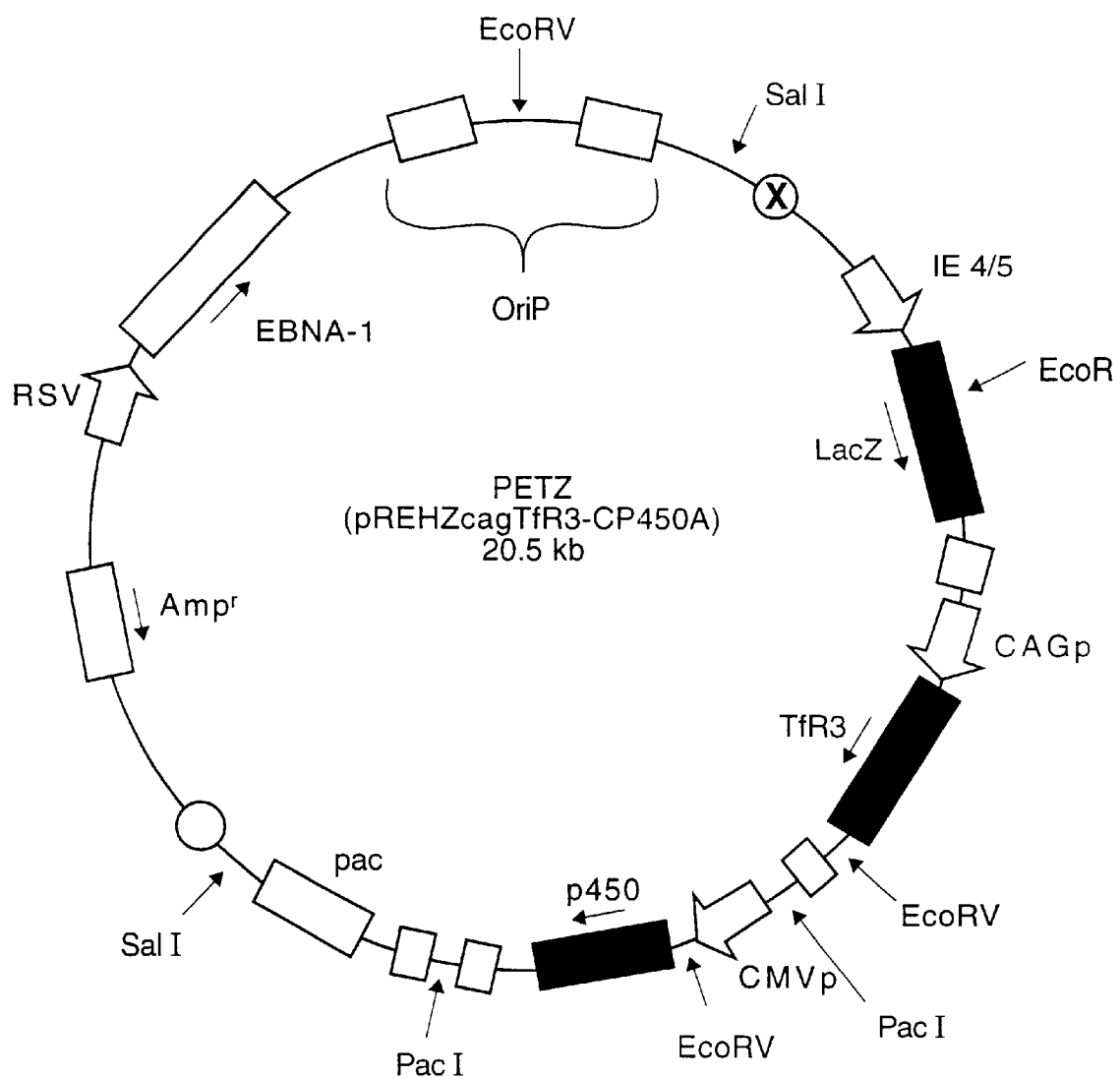
FIG. 8 is a representation of an amplicon PETZ used in examples described herein.
Figure 9A:
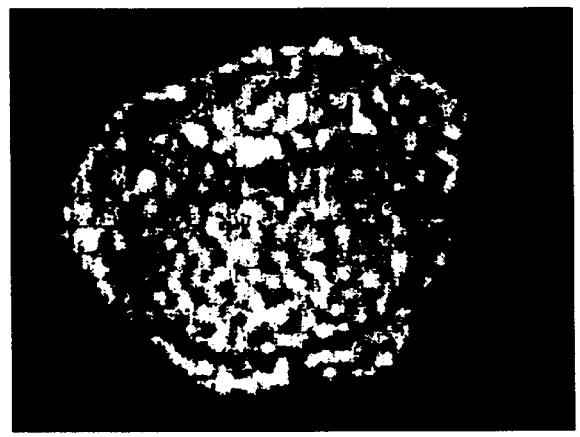
FIGS. 9A to 9C are a series of in vivo magnetic resonance images of a coronal view of a mouse brain containing bilateral brain tumors.
Figure 9B:
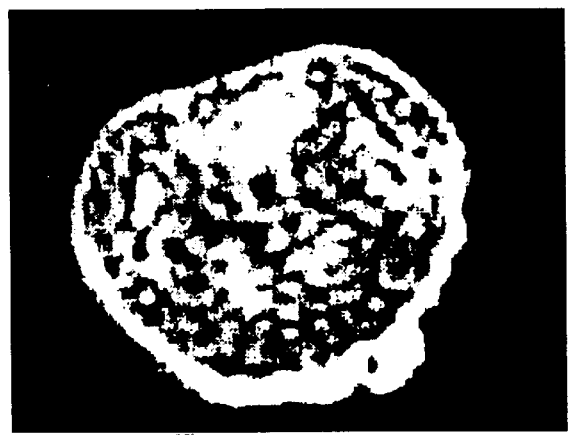
Figure 9C:
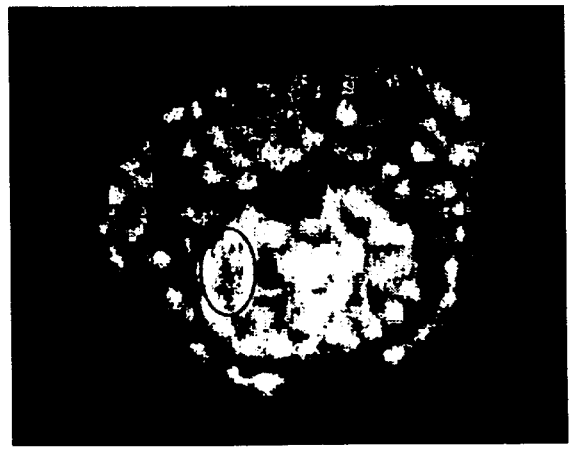

In another example of imaging of in vivo gene transfer, Gli36EGFR cells were implanted into nude mice 8 days prior to imaging to generate bilateral frontal tumors. On day 6 after implantation, tumors on the right were infected with the HSV-based amplicon PETZ (FIG. 8), which drives expression of an altered form of the TfR. Forty-eight hours after virus administration animals were imaged without contrast agent (T1-weighted pre-contrast scan; FIG. 9A) and then injected with Tf-SPDP-CLIO. Three images were acquired: (1) prior to contrast agent (FIG. 9A); (2) a conventional imaging agent, Omniscan®, was administered and mouse images were again acquired for anatomical resolution (T1-weighted MRI after administration of Omniscan; FIG. 9B); and (3) 24 hours after contrast agent injection (24 hour 3-D gradient echo; FIG. 9C) in which an ellipse shows the tumor infected with PETZ amplicons as a dark mass in the right half of brain; also note co-localization with Omniscan® images of tumors (lighter region) in FIG. 9B). These results indicate that gene therapy can be imaged in vivo.

All contrast agents were injected by tail-vein administration (1 mg/kg Tf-SPDP-CLIO). Scans: (9A) T1 SE 300/16, FOV 8 cm, 256×256, 1.9 thk/0.2 spc; (9B) T1 SE [Omniscan], and (9C) T2 3D GR 38/20/5°, FOV 10 cm, 256×256, 0.5 thk/0.0 spc. [Tf-SPDP-CLIO.

Example 6

Correlation of Gene Expression with Magnetic Properties

Gene expression can be correlated with the MR signal by transfecting U87δEGFR human glioma cells with the amplicon vectors described herein and quantitating gene expression. The amplicons can also be tested in other cell lines (MCF7 breast adenocarcinoma, BT20 undifferentiated breast adenocarcinoma, LX1 small cell lung carcinoma and LS174T colon adenocarcinoma).

U87δEGFR cells are grown in RPMI 1640 medium supplemented with 10% FBS. Other cell lines are grown as monolayers in Minimum Essential Medium (MCF-7) or RPMI 1640 (LX-1, LST174T) supplemented with 10% FBS (all media and sera from Life Technologies, Gaithersburg, Md.). Cells are kept at 37° C. in a humidified 6% $CO_2$ atmosphere. Upon reaching confluency, cells are split; medium is renewed twice a week. Western blotting is used to quantitate gene expression. The above listed human cell lines ($10^5$ cells) are transduced with $10^6 10^9$ TU of HSV/EBV amplicon containing the different inserts. Twelve to 96 hours after transduction, cells are lysed in 0.5 ml of 50 mM Tris/HCl pH 6.8, 0.1% SDS , 0.1% Igepal supplemented with 1 mM PMSF and Complete Inhibitors TM (Boehringer Mannheim, Indianapolis, Ind.). The lysates are sonicated on ice for 1 minute and then centrifuged at 14,000 g for 10 minutes. Twenty $\mu$l of the supernatant is loaded on 7.5% SDS-PAGE gels and following electrophoresis for 60 minutes at 120 V is transferred (150 mA, 90 minutes) onto PVDF membranes (Bio-Rad, Hercules, Calif.). Membranes are blocked for 1 hour at room temperature in PBS pH 7.4, 1% defatted milk, 0.1% Tween 20, and then incubated with 1:500 dilutions in blocking buffer of either rabbit polyclonal anti-ETR (Boehringer, Mannheim) or anti-Tk antibodies for 2 hours. Following incubations with 1:1,000 dilutions of biotinylated isotype matched antibodies (Pierce, Rockford, Ill.) and avidin-peroxidase (Bio-Rad, Hercules, Calif.) for 60 and 30 minutes respectively, blots are developed in Luminol/H202/p-iodophenol (Amersham Life Sciences, Arlington Heights, Ill.) for 30 seconds. The chemiluminescent signals are quantitated by densitometric analysis using public domain software NIH Image 1.60 for 1-D gels. As an internal control and reference for the expression, a known amount of GFP (Clontech, Palo Alto, Calif.) is included in each gel. Empty amplicons are used as a negative control.

Gene expression (ETR, Tk) is analyzed by Western blotting and displayed as 1) type of construct, 2) a function of time, 3) amount of virus (TU—Transducing units) used for transfection, and 4) cell line. The data is used to select the construct in which ETR expression most closely correlates with expression of TK. If gene expression is low alternative dual CMV promoters can be used to drive the marker genes.

Example 7

Correlation of ETR Expression with Cellular $^{125}$I-Tf-CLIO Internalization and Magnetic Properties The correlation between expression of ETR, cellular uptake of $^{125}$I-Tf-CLIO, and MR signal intensity of cells constitutively expressing ETR can be established by use of U87δEGFR human glioma cells grown in RPMI 1640 medium supplemented with 10% FBS. Cells are transduced with the optimized HSV/EBV vector, which will be added at a MOI=3 in minimal volume (400 $\mu$l per 10 cm dish), to allow for infection of a maximum number of target cells. Dishes are then placed at 37° C. in an atmosphere containing 5% $CO_2$. At different time points later, the medium is replenished with an additional 10 mL. Transduced cells ($10^6$ cells/well) are incubated with freshly prepared $^{125}$I-Tf-CLIO at various concentrations in serum free DMEM (37° C. for 1 hour). Cells are washed 3 times in HBSS and lysed in 0.5 ml 1% Triton® X-100, 1 mM EDTA, pH 8 prior to radioactivity, protein, and fluorescence determination.

The positive control is a stably transfected 9L 3.9 clone constitutively overexpressing ETR. Cells transfected with different TU's are incubated with a surplus of $^{125}$I-Tf-CLIO (amount determined by saturation kinetics) for one hour and washed extensively. Cellular radioactivity is determined by gamma counting (Wallach, Turku, Finland), fluorescence. The quantitative experiments are performed for 1) different amounts of TU (dose response), and 2) different time of analysis after CLIO-Tf probing (time response).

Transduced cells probed with $^{125}$I-CLIO-Tf according to the above variables are embedded in low melting agarose and subjected to MR imaging according to previously established protocols. Non-transduced cells serve as a negative control and ETR+ cells as a positive control. Briefly, $10^5$ cells are embedded in 30 µl low melting agar to prevent drying and susceptibility artifacts. Each pellet is then sealed in a well with an additional 0.5 mL of agarose. MR imaging is performed with a 1.5 T superconducting magnet (Signa 5.0; GE Medical Systems, Milwaukee, Wis.) using a 5-inch surface coil as described herein.

The above data are used to correlate cellular TfR expression with $^{125}$I-Tf-CLIO internalization and MR signal intensity of transduced cells. Signal intensity is plotted against TU's used for transduction. Calibration curves are also obtained by using cell mixtures with known % of ETR+ cells mixed with ETR– cells. Analysis of transduced cell lines used the calibration curves and quantitative RT-PCR determinations of cell pellets.

Figure 10A:
FIGS. 10A and 10B are in vitro magnetic resonance images of a top view of cell pellets infected with an HSV-based amplicon and containing varying concentrations of the contrast agents Tf-MION and Tf-SPDP-CLIO, respectively.
Figure 10A:
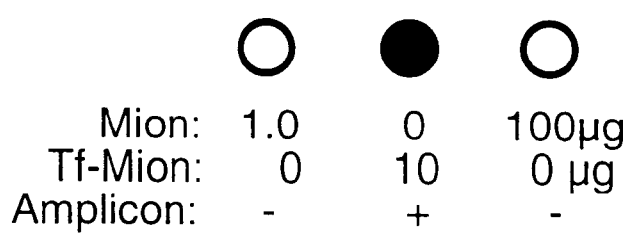
Figure 10B:
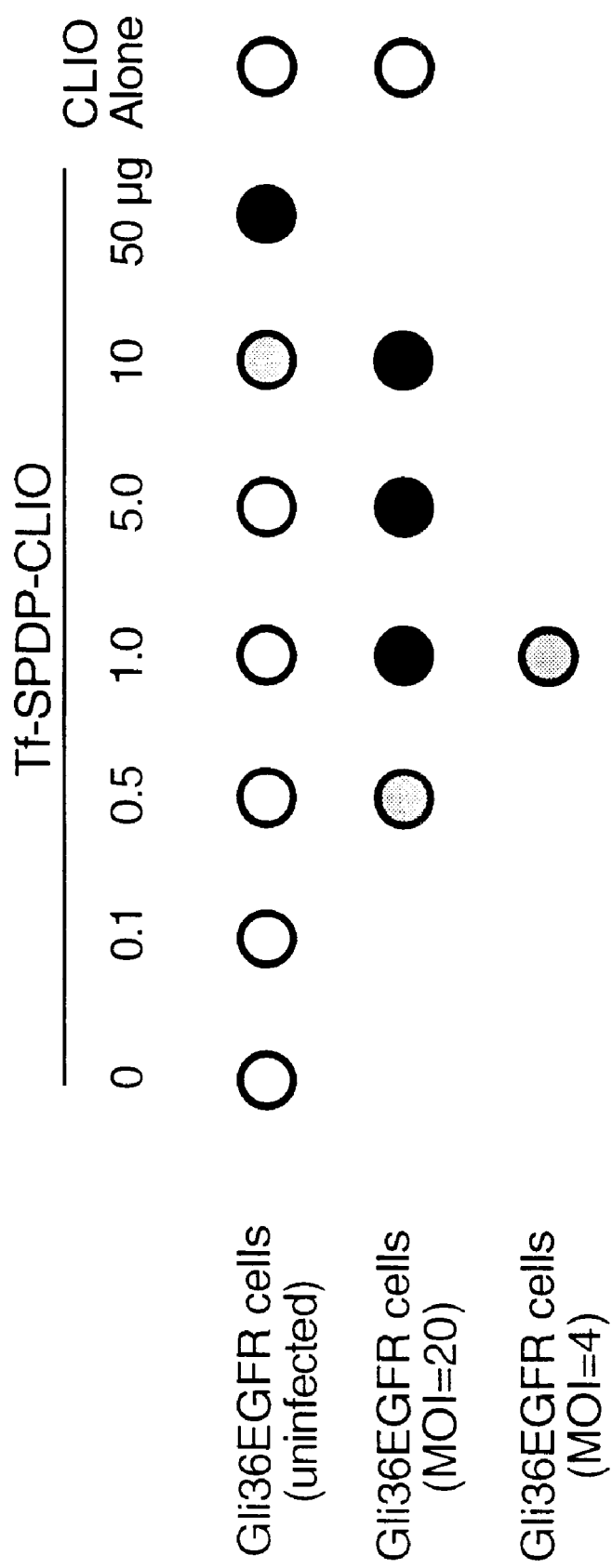

In another experiment, in vitro infection of cells with an HSV amplicon expressing TfR was shown to significantly alter MR signal intensity. Uninfected Gli36#6 were incubated with increasing concentrations of Tf-MION (see, top row of FIG. 10A). In this figure, concentration labels refer to the amount of iron molecules added to the sample. For one concentration of Tf-MION, 10 µg, cells were infected with an amplicon (PETZ, in FIG. 8) driving expression of TfR and LacZ. Following infection, the cells were allowed to recover and were washed, pelleted, and imaged at room temperature as follows: SE (Spin Echo): TR 3000 ms, multiecho with TE 25, 50, 75, 100ms. Slice thickness 1.9 mm, field of view 8 cm, matrix 256×256, 2 NEX, scan time 26:12 minutes. As shown in the lower half of FIG. 10A, expression of TfR due to infection dramatically altered the MR signal in the center cell pellet.

In another similar experiment, in vitro MR imaging was used to analyze viral transfer of the transferrin receptor and labeling with Tf-SPDP-CLIO. Gli36EGFR cells were uninfected or infected with an HSV-based amplicon (PETZ) driving expression of an altered form of the transferrin receptor (Multiplicity of Infection (MOI) of 20 or 4). After 24 hours, the cells were incubated with the indicated concentrations of Tf-SPDP-CLIO for 2 hours at 37° C. Following incubation, cells were harvested, washed, and pelleted for imaging at room temperature. As a control for non-specific uptake of unconjugated CLIO, infected and uninfected cells were also incubated in a similar fashion with 50 µg of CLIO alone. Concentration numbers along the top of the figure refer to the amount of iron added to the sample in the form of Tf-SPDP-CLIO. The ratio of Tf conjugated to CLIO for Tf-SPDP-CLIO was 4:1. Note the dramatic change in MRI at lower concentrations of iron following infection with amplicons expressing the altered transferrin receptor, especially at an MOI of 20. The MR imaging conditions were as follows: SE (Spin Echo); TR 3000 ms, multiecho with TE 25, 50, 75, 100 ms. Slice thickness 1.9 mm, field of view 8 cm, matrix 256×256, 2 NEX, scan time 26:12 minutes.

Example 8
Correlation of Cellular CLIO Uptake with Ganciclovir Toxicity

Tk (thymidine kinase) is a prodrug converting enzyme that converts the relatively inert prodrug ganciclovir to toxic triphosphate ganciclovir and is currently in clinical trials for this use. Cellular Tf-CLIO internalization can be correlated with Tk expression and thus ganciclovir toxicity in U87δEGFR cells.

U87δEGFR cells are grown as described above and transduced with the HSV/EBV amplicon containing Tk/TfR using the optimized protocol. Twenty-four to 48 hours after transfection, cells are aliquoted and 1) incubated with $^{125}$I-Tf-CLIO to determine uptake, or 2) tested for ganciclovir toxicity. Positive controls consist of stably transfected U87δEGFR cells overexpressing Tk and ETR, and negative controls consist of non- or mock transfected cells.

Functional expression of Tk in transduced cells is determined by ganciclovir sensitivity measurements. Cells are seeded in 96 well plates and grown for 24 hours. The medium is replaced daily with ganciclovir supplemented medium at different concentrations (Syntax Laboratories, Palo Alto, Calif.). $^3$H thymidine accumulation studies are performed in triplicate on the third day to measure cell proliferation. Cells in each well are exposed to thymidine for 4 hours at a concentration of 0.5 µCi/well. Cells are collected on glass filter paper with a cell harvester, solubilized with Soluene™ 350 (Packard, Meriden, Conn.), and mixed with Instafluor scintillation mixture to determine the dpm/well using a Packard B1600 TriCarb™ spectrometer. Radioactivity in each well is expressed as a percentage of control (without ganciclovir).

Cellular Tf-CLIO uptake and ganciclovir toxicity are correlated by plotting the two parameters against each other.

Alternative systems such as p450/reductase (CPA) and/or carboxylesterase (CPT-11) and/or cytosine deaminase (CD) can also be used.

Example 9
Use of Amplicons to Kill Cancer Cells

Figure 11:
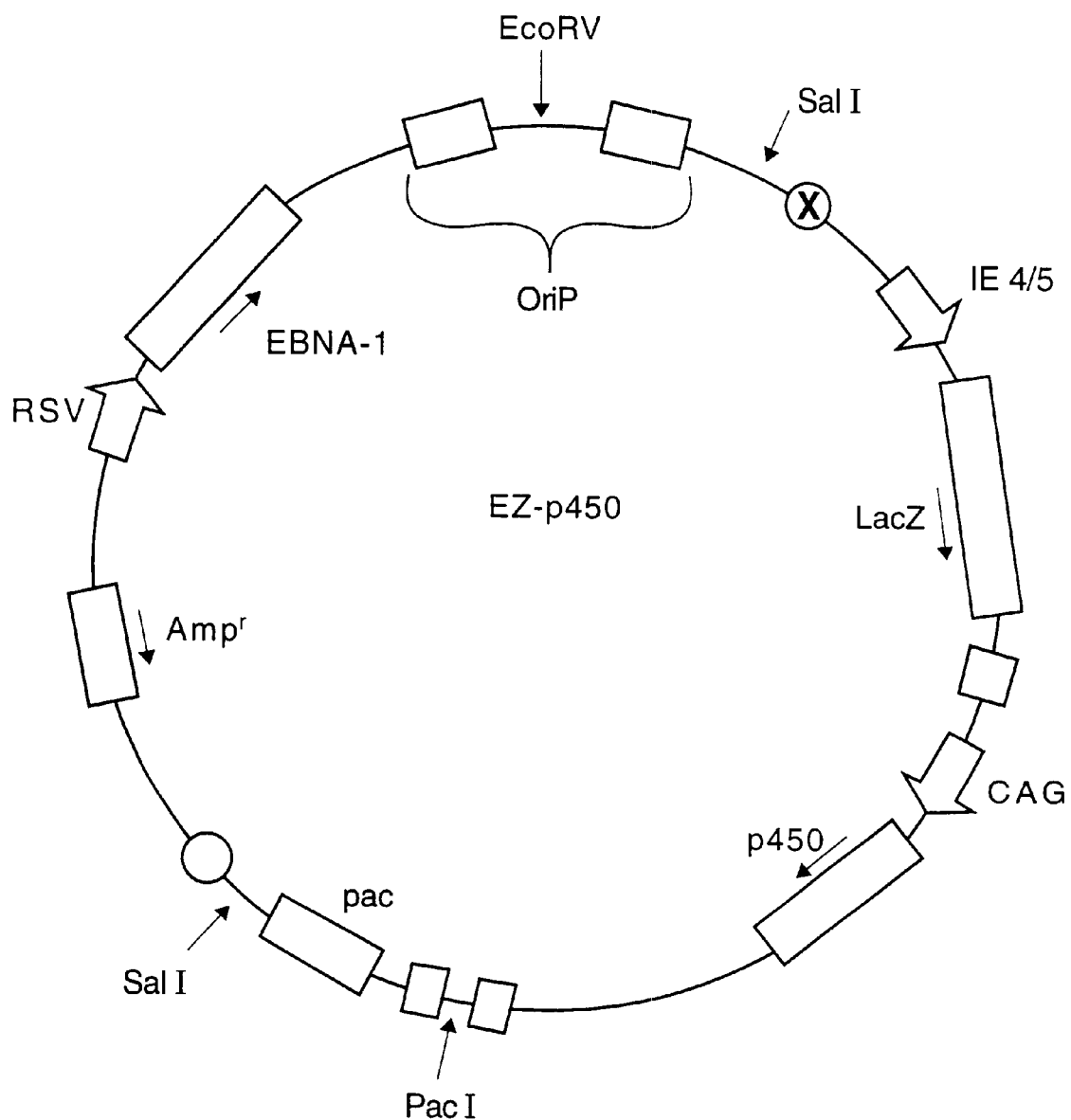
FIG. 11 is a representation of an amplicon EZ-p450 used in examples described herein.
Figure 12:
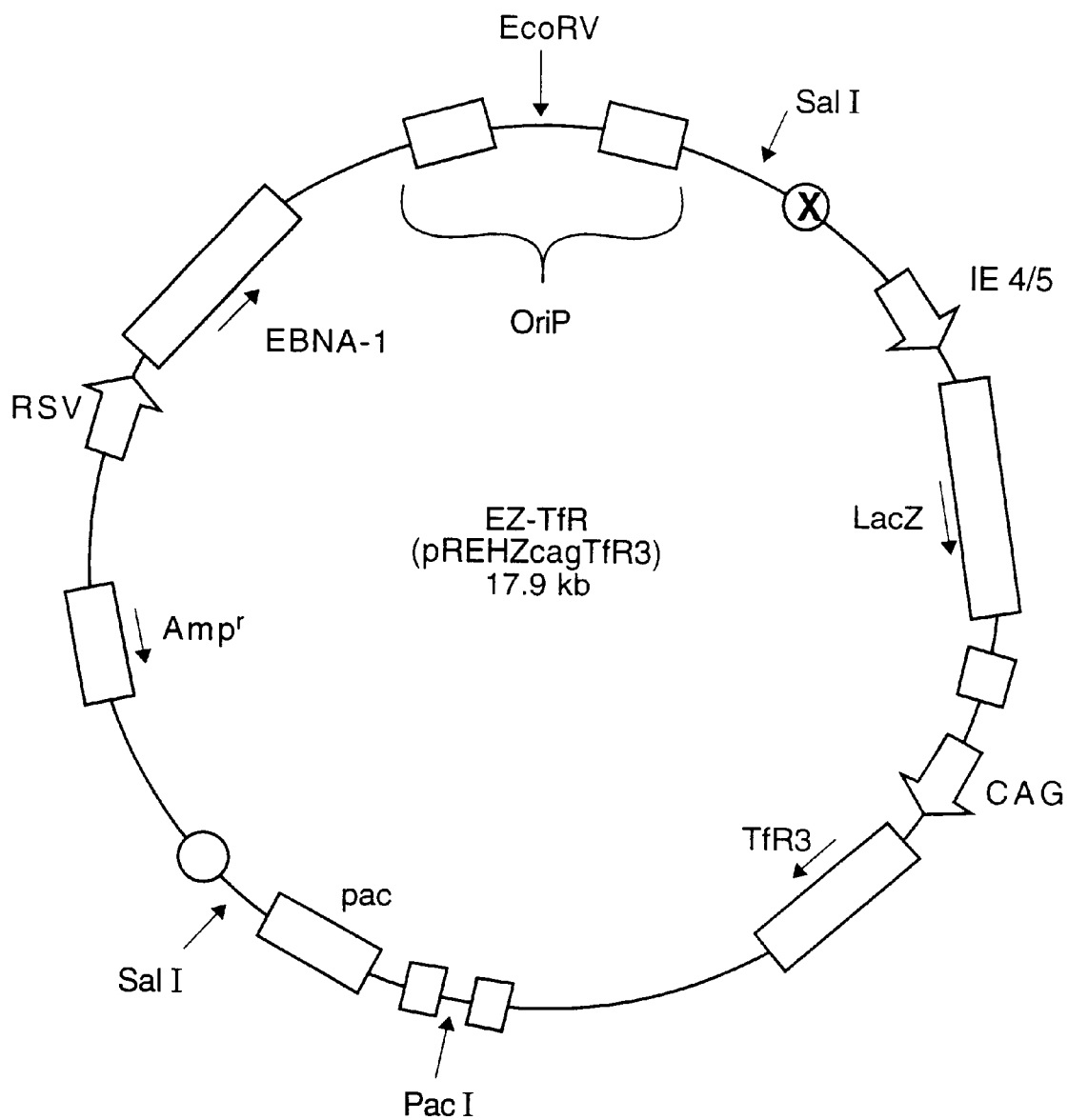
FIG. 12 a representation of an amplicon EZ-TfR used in examples described herein.
Figure 13:
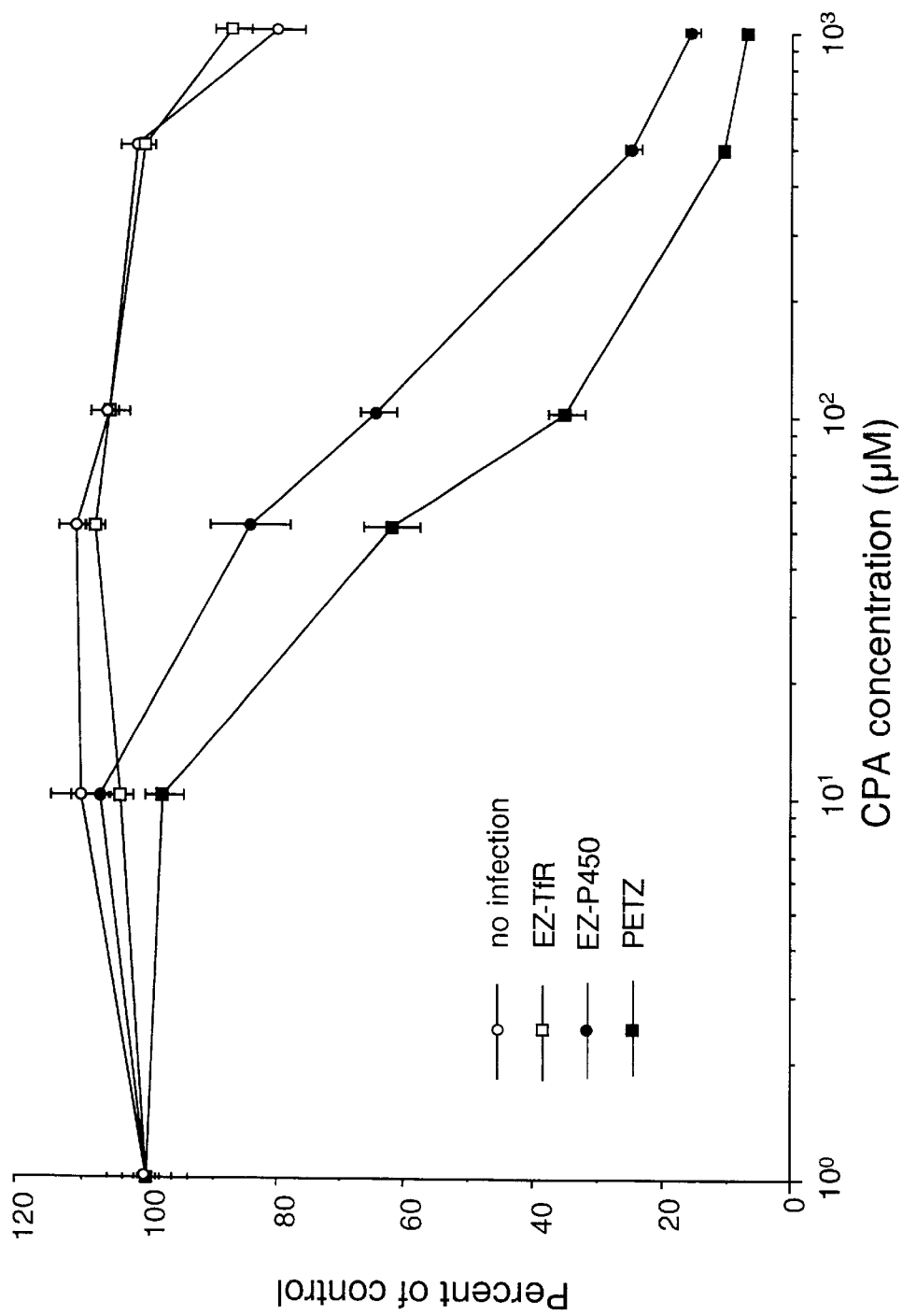
FIG. 13 is graph showing percentage of cancer cells surviving after infection with various amplicons described herein and exposure with cyclophosphamide (CPA).

Cancer cells were destroyed using a PETZ vector expressing p450 (FIG. 8) and an EZ-p450 vector also expressing p450 (FIG. 11). Gli36EGFR cells were plated at approximately 10% confluency. Cells were infected the next day (MOI=5) with either one of three amplicons: EZ-TFR (FIG. 12), which was a control having a transferrin receptor gene, but lacking a p450 gene; EZ-p450 (FIG. 11), which was a second control with a p450 gene but no transferrin receptor gene; or PETZ (FIG. 8), which includes both the p450 and transferrin receptor genes. Following a 24 hour incubation with the viral amplicons, cyclophosphamide (CPA) was added in varying concentrations as indicated in the graph of FIG. 13. CPA is a chemotherapeutic compound that is metabolized by the expression product of the p450 gene (cyp2B1 in the rat). Cleavage of CPA yields an active metabolite, which is toxic to the cancer cells. Cell number was measured 72 hours later using a Coulter Counter. The data are presented in the graph in FIG. 13 as a percentage of control, where control cells are virally infected cells in the absence of CPA.

As shown in the graph in FIG. 13, both the PETZ and EZ-p450 amplicons significantly increased cell killing starting at a CPA concentration of $10^1$ µM. At a concentration of $10^3$ µM, less than 10 percent of control cells were alive (PETZ) compared to about 80 percent for the controls of no amplicon or the EZ-TFR amplicon. These results indicate that the p450 gene is expressed in the cancer cells, and activates CPA in a normal fashion. The PETZ vector includes the TfR gene, and thus also induces the expression of TfR on the surface of the cancer cells to allow imaging of these cells.

Example 10
In vivo Imaging of ETR/TK Gene Expression

Gene expression (ETR, TK) can be imaged in vivo using U87δEGFR human gliomas transplanted into nude mice. U87δEGFR cells are grown subcutaneously or orthotopically in nude mice and gene transfer of TK genes is performed by direct intratumoral injection of the amplicon vector. Tumors thus treated are then processed for 1) Western blotting and 2) immunohistochemistry. These data are used to establish transduction protocols that are used for MR imaging of gene expression.

U87δEGFR cells are grown in RPMI with 10% FBS and supplemented by G148. Nude mice are implanted with $10^5$–$10^6$ cells subcutaneously in both flanks. When tumors have grown to 8–10 mm in size, animals are re-anesthetized and the amplicon is directly injected into the tumor on one side while the contralateral tumor serves as a negative control. At variable time points (24, 48, 72, 96 hours) after amplicon injection, animals (n=5 in each group) are sacrificed and tumors are removed. Specimens are used for 1) determination of Tk expression by Western blotting, and 2) immunohistology to determine the spatial Tk and ETR expression.

Tissue preparation for Western blotting follows established procedures. All procedures are performed on ice. Tumor tissues are cut to pieces of approximately 1 mm$^3$ using a scalpel blade. A maximum of 100 mg of tumor is then transferred into a 2 ml screw cap Eppendorf tube, half-filled with 1 mm glass beads, and 1 ml extraction buffer (20 mM Tris pH 8.0, 150 mM NaCl, 5 mM EDTA, 0.5% Triton X-100). Extraction is performed in a BeadBeater® in 20 second bursts at maximum speed. In between, the extraction process is visually monitored and the samples cooled on ice. The homogenate is finally transferred into a new Eppendorf tube and spun for 10 minutes at 16000×g. The supernatant is aliquoted and stored at −70° C. until further use. Protein contents are determined with the BCA assay and Western blotting performed as described above.

The distribution of Tk is determined by immunohistochemistry. Tissue sections are obtained using a cryostat. A horseradish peroxidase (HRP)-conjugated anti-rat monoclonal antibody (Vector Laboratories; Burlingame, Calif.) is reacted with the section for 30 minutes at RT followed by 3,3'-diaminobenzidine tetrahydrochloride (DAB)-staining for 10 minutes. Sections are hematoxilin counter-stained (30 seconds), dehydrated through graded ethanol (50%–100%) and xylene, dried and mounted. Images are analyzed using an Axiovert 100TV microscope (Wetzlar, Germany).

The above data is used to determine the efficacy of gene expression in vivo in tumors. Data is used to directly correlate Tk and ETR expression.

Example 11
Correlation of Topography and Level of Gene Expression

The hybrid HSV/EBV vectors described above can be used to correlate the topography and level of ETR gene expression. U87δEGFR cells are grown in DMEM and implanted into nude mice (n=40 total) either subcutaneously (ectopic) as described or intracerebrally (orthopic). For the latter, nude mice are anesthetized with 9 mg/100 g ketamine and 0.9 mg/100 g xylazine IP. Their heads are immobilized and using aseptic technique, a 1 mm burr hole is drilled into the right side of the skull 1 mm anterior, 1 mm lateral, and 2.5 mm ventral to the bregma. A Hamilton 10 µl gas-tight syringe (Hamilton Comp., Reno, Nev.) is used to inject $10^5$ cells into the right frontal lobe. The injection occurs slowly over 5 minutes, and the needle is slowly retracted for an additional 5 minutes. The burr hole is occluded with bone wax to prevent leakage of CSF, and the skin is closed with staples, which are removed prior to MR imaging.

Ten days after tumor implantation, animals are used to deliver the HSV/EBV amplicon vector by direct tumor injection (tumors take up the amplicon by endocytosis. Tumoral ETR expression is probed for 24 hours after IV administration of Tf-CLIO. Imaging is performed at 1.5 T when spatial resolution is not critical (phantoms, peripheral tumors) and at 7.1 T when high resolution is required. The imaging parameters at 1.5 T are similar to the ones used above (GE Signa 5×, General Electric, Waukesha, Wis.). Imaging parameters are chosen to acquire images with T2, T2* and T1 weighting.

In case intratumoral gene expression is too localized to the needle tract, intraarterial delivery of the amplicon can be used. This is done by retrograde perfusion through the carotid artery, however in nude rats rather than in mice. Briefly, animals are anesthetized and the left and right common and external carotid arteries (ECA) are exposed through a ventrolateral cervical incision. After ligation of the pterygopalatine artery and proximal external branches (superior thyroidal and occipital arteries), a polyethylene catheter (PE-10, Clay Adams, Parsippany, N.J.) filled with heparinized saline is inserted into the right or left ECA and its tip advanced to the bifurcation of the CCA for retrograde infusion into the ICA. Using a constant-flow infusion pump (Harvard Apparatus, Inc.; South Nantucket, Mass.), rats are infused with viral suspension at a rate of 0.12 mL/sec. Animals are allowed to recover and receive an IV injection of Tf-CLIO 24–48 hours after the vector followed by MR imaging or sacrifice 24 hours later.

In another similar experiment, Gli36 clone 4 cells were infected with a herpes (HSV) amplicon (PETZ) expressing both ETR and LacZ from different promoters. Following infection, cells were allowed to recover and at the indicated time points cells were lysed and equal amounts of cell lysates were analyzed by Western blot using antibodies specific for either ETR or LacZ as described herein. The LacZ-specific antibody was a rabbit polyclonal antibody obtained from Chemicon Inc. The anti-TfR antibody is described in Warren et al., *J. Biol. Chem.*, 272:2116, 1997.

Figure 14B:
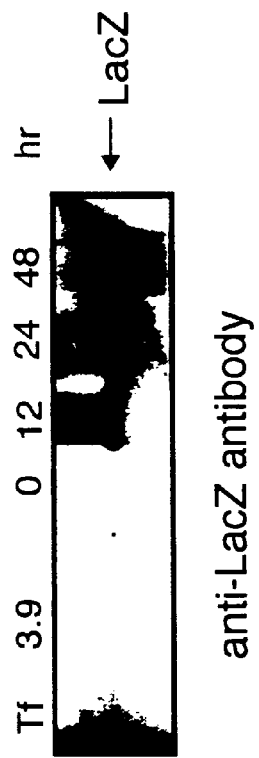
FIGS. 14A and 14B are images of Western Blot assays showing the correlation of the increase in expression over time of the ETR gene and the LacZ gene, respectively.
Figure 14A:
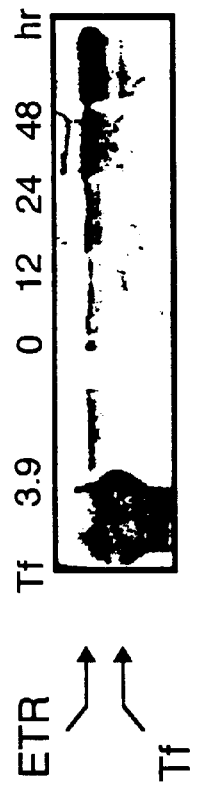

As shown in FIG. 14A, an anti-TFR/TF antibody showed a steady increase in expression of the ETR protein over time up to 48 hours (when the last measurement was made). 3.9 rat cells were used as a positive control, because they express a constant level of the transferrin receptor. Similarly, FIG. 14B shows a steady increase in the expression of the LacZ protein over time up to 48 hours. These results indicate a direct correlation between the increase in the expression of ETR and LacZ.

In addition, immunofluoresence was assessed, using FITC-anti-TfR and Rd-Anti-LacZ, to demonstrate that both transgenes were expressed in each cell, rather than individual cells expressing only one of the genes (immunofluorescence staining data not shown). These results confirm a direct correlation between the increase in the expression of ETR and LacZ in the same cell.

Example 12
Monitoring Treatment Response of Ganciclovir Treated Tumors Using MR Imaging The new methods can be used to monitor the anti-tumoral efficacy of drug treatments. U87δEGFR cells are transfected with the amplicon and select stable clones overexpressing transgenes. These cells, designated as U87δEGFR/Tk/ETR are implanted into nude mice and MR imaging is performed (after IV administration of Tf-CLIO) in mice treated with different regimens of ganciclovir.

Briefly, U87δEGFR cells are plated on a 10 cm Petri dish (Becton Dickinson Labware, Franklin Lakes, N.J.) in DMEM supplemented with 10% FBS ($10^6$ cells/dish) 24 hours before transduction. The amplicon will then be added and washed after 1 hour of incubation. Twenty-four to 72 hours later the cells will be subcultured at a 1:6 ratio into selection medium (DMEM with 10% FBS, containing 1mg/ml of Ampicillin. After 3 weeks of selection, positive clones will be selected by cylindrical cloning. Stable transfected cells will be maintained in culture as described above and periodically tested for transgene expression.

The produced tumor cells will then be implanted into nude mice (flank, brain) and divided into three groups (n=10 each; n=30 total): 1) no treatment, 2) ganciclovir 10 mg/kg b.i.d. for 5 days and 3) ganciclovir 50 mg/kg b.i.d. for 5 days. Animals will receive Tf-CLIO IV after the last treatment and will be imaged by MR at 1.5 T 24 hours later using the above described (section D2.2) imaging protocol. Animals will be sacrificed immediately after imaging and tumors will be excised and processed for correlative immunohistology.

The above imaging data allows the correlation between signal intensity and treatment response as determined by Tk presence and tumor size. The control group also allows the testing of homogeneity of Tk and ETR expression in vivo.

Example 13

Efficacy of Different Reporter Complexes

Figure 15:
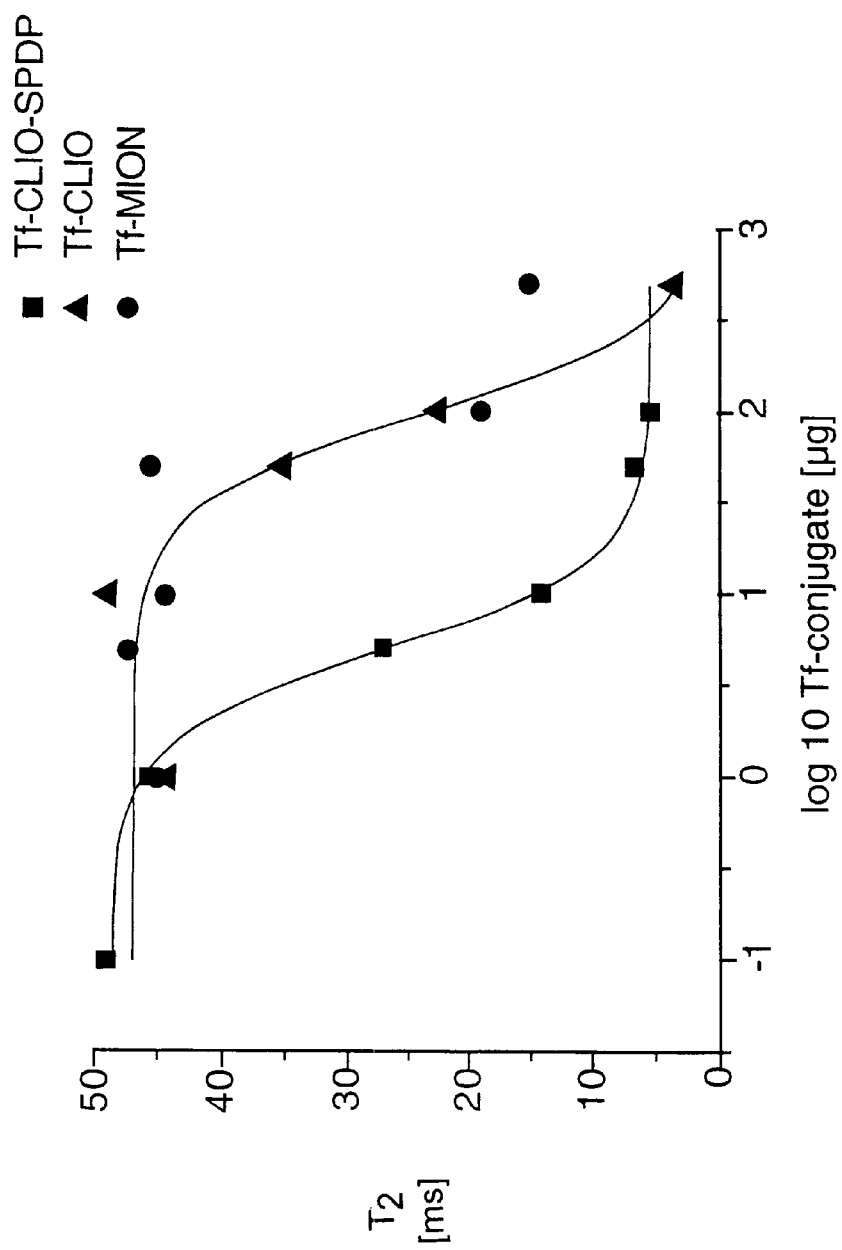
FIG. 15 is a graph showing magnetic resonance imaging efficacy for three different reporter complexes.

The efficacy of the various reporter complexes was tested. A rat glioma cell line (9L3.9), which stably overexpresses an altered form of the human transferrin receptor, was incubated with different concentrations of reporter complexes (Tf-SPDP-CLIO (■), Tf-CLIO (▲), or Tf-MION (o)) for 2 hours. Following incubations, cells were harvested, washed, and pelleted for imaging. In vitro magnetic resonance imaging was carried out using spin echo sequences with variable TE to calculate T2s. In the graph in FIG. 15, the leftward shift in T2 vs iron concentration indicates an increased sensitivity for detection by MRI. As shown in this figure, the reporter complex Tf-SPDP-CLIO provides the highest sensitivity for MRI detection (most left shift), but the other two reporter complexes also provide an increased sensitivity. The imaging conditions were as follows: GE Signa 5.x (General Electrics), 1.5 Tesla, 5-inch surface coil, SE (Spin Echo): TR 3000 ms, multiecho with TE 16, 20, 25, 32, 40, 50, 60, 75, 80, and 100 ms. Slice thickness 1.9 mm, field of view 8 cm, matrix 256×256, 2 NEX, scan time 26:12 minutes.

Example 14

Mutagenesis of ETRs

The goal of this mutagenesis is to construct different versions of the ETR each containing mutations that have been reported to increase receptor internalization rates (see, e.g., Pytowski et al., *J. Biol. Chem.*, 270(16), 9067–73, 1995; and Alvarez et al., *J. Biol. Chem.*, 265(27), 16644–55, 1990).

The original ETR construct will be altered by site directed muatagenesis to generate a family of individually mutated ETRs (mutETR) with putatively increased internalization rates. Two single amino acid changes (Gly31Tyr and Ser34Tyr) and two double amino acid changes (Cys62Ala:Cys67Ala and Cys62Ser:Cys67Ser) are made to ETR. The four new receptor mutants are called mutETR31Y, mutETR34Y, mutETR6267A, and mutETR6267S. Following mutagenesis rat 9L glioma cells stably expressing each construct are isolated and the level of receptor expression quantified by Western blot.

The methods to perform all the mutagenesis, cell line isolation, and assessment of mutETR expression levels all use standard techniques.

Next, Tf-MION binding, Tf-MION internalization rate, and total Tf-MION accumulation in cells expressing different mutETRs are measured and compared to the same factors in cells expressing unaltered ETR.

To determine the extent of Tf-MION accumulation in the cells, either control cells or cells expressing different mutETRs are grown as described previously (Moore et al., *Biochemica Biophysica Acta*, 1402, 239–249, 1998).

The cells are then washed and incubated with radiolabeled Tf-{$^{111}$In}MION (TF in the form of holo-Tf) at 4 μg/ml for 60 minutes at 4° C. The cells are then warmed to 37° C. to initiate intracellular and cell surface receptor redistribution. At sequential time points the cells are washed three times at 4° C. with isotonic saline and incubated for 5 minutes at 4° C. with 0.5M NaCl/0.2 M acetic acid to remove surface-bound Tf-MION (White et al., *Cancer Research*, 50, 6295, 1990). Accumulation of acid-resistant internalized {$^{111}$In}MION is quantified by scintillation counting and expressed as a function of time. The level of receptor expression on the cell surface is measured by incubating the cells with Tf{$^{111}$In}MION for 60 minutes at 4° C., washing the cells 3 times at 4° C. with saline and then counting cell associated radioactivity directly. Total cellular binding is determined by incubating the cells as described and then warming them to 37° C. until steady state receptor distribution has occurred (approx. 45 minutes incubation at 37° C.), followed by 3 sequential washes of the cells with 4° C. isotonic saline and scintillation counting.

To determine non-specific binding, these studies are also performed in the presence of a 100-fold excess of either unlabelled Tf-MION, unlabelled Tf, or unlabelled MION alone. These data will allow comparison of the mutETRs receptor internalization rates to the rates of unaltered ETRs. Additionally the measurement of total cell associated MIONs will allow correlation of changes in Tf-MION cell surface binding and internalization rates with increases in the cell-associated MIONs.

The effect of mutETRs on MR signal intensity is determined by using MR phantoms. The goal of this experiment is to determine whether mutETR-dependent increases in cellular uptake of Tf-MION will increase MR signal intensity resulting in greater MR sensitivity.

MutETR cell lines displaying increased receptor internalization rates and increased Tf-MION accumulation are probed with [$^{125}$I]Tf-MION, embedded in low melting point agarose, and subjected to MR imaging according to previously established protocols as described above. As controls, both mock-transfected and ETR expressing cells are also probed. The minimum number of probed cells required to generate MR signal is determined by mixing known percentages of mutETR+ (or ETR+) cells with ETR– cells and subjecting the phantoms to MR imaging. Cell mixtures are normalized to the steady state expression level of receptor mutants. The cellular accumulation of Tf-MION is also measured by gamma counting to precisely correlate accumulated Tf-MION levels to MR signal intensity.

The above data are used to correlate increased cellular accumulation of [$^{125}$I]Tf-MION with MR signal intensity of transduced cells. Signal intensity is plotted against number of cells expressing mutETR and compared to curves generated using ETR expressing cells. These data identify receptor mutations that result in increased cellular accumulation of Tf-MION and altered MRI signal intensity.

Mutations from different favorable mutETR candidates are combine as follows to determine whether their combination provides further increases in receptor internalization rates and cellular accumulation of MION.

Based on the above data, mutations identified as increasing cellular accumulation of MION and MR signal intensity are combined in a single mutated ETR construct. Depending on the number of mutETRs that increase cellular MION uptake, more than one mutETR with different combinations of mutations are made. Cell lines stably expressing these constructs are isolated and characterized as described above.

Next, the cumulative effects of multiple ETR mutations on biological properties of the receptor and MR signal intensity are analyzed to determine whether combining mutations that individually increase cellular accumulation of MIONs are detrimental for accumulation or result in an additive or even synergistic increases in MION accumulation. Analysis will be identical to the procedures described above. The final step in these studies is to associate the changes in receptor internalization and cellular accumulation of MIONs with alterations in MR signal intensity. These studies are performed as described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of indicating expression of a specific gene in vivo in a subject, the method comprising
 introducing a nucleic acid encoding an internalizing transferrin receptor and the specific gene into cells in the subject, wherein when the internalizing transferrin receptor is expressed, the specific gene is also expressed;
 administering to the subject a reporter complex comprising a transferrin receptor-specific moiety linked to a reporter group, wherein the reporter complex binds to internalizing transferrin receptors expressed on the cells; and
 imaging the subject to monitor the reporter complex as an indication of expression of the specific gene.

2. The method of claim 1, wherein the nucleic acid encoding the internalizing receptor is in a viral or nonviral vector.

3. The method of claim 1, wherein the specific gene is a therapeutic gene.

4. The method of claim 1, wherein the specific gene encodes an enzyme.

5. The method of claim 1, wherein the reporter complex comprises transferrin linked to one or more magnetic, paramagnetic, or super paramagnetic nanoparticles.

6. The method of claim 1, wherein the reporter group is a magnetic particle, an optically detectable molecule, or a radioisotope.

7. The method of claim 1, wherein the nucleic acid encoding the internalizing receptor is genetically modified to increase the utility of the internalizing receptor for imaging.

8. The method of claim 7, wherein the modification is designed to alter recycling of the receptor, internalization, ligand affinity, or receptor half-life within the cell.

9. The method of claim 1, wherein the reporter complex comprises one or more cross-linked iron oxide nanoparticles (CLIOs).

10. The method of claim 1, wherein the reporter complex comprises one or more monocrystalline iron oxide nanoparticles (MIONs).

11. The method of claim 1, wherein imaging is magnetic resonance imaging, NMR spectroscopy, or nuclear imaging.

12. A nucleic acid construct comprising
 a nucleic acid sequence encoding an internalizing transferrin receptor; and
 a nucleic acid sequence encoding a therapeutic protein.

13. The construct of claim 12, further comprising one or more regulatory sequences.

14. The construct of claim 13, wherein the regulatory sequence comprises a promoter.

15. The construct of claim 14, wherein the promoter induces expression without regulation by environmental conditions within a cell.

16. The construct of claim 13, wherein the one or more regulatory sequences comprise two promoters that are the same or different.

17. The construct of claim 12, wherein the nucleic acid encoding the receptor is genetically modified.

18. A viral or nonviral vector comprising the nucleic acid construct of claim 12.

19. A kit for imaging expression of a specific gene in vivo, the kit comprising a nucleic acid construct of claim 12; and
 a reporter complex comprising a receptor-specific moiety and a reporter group, wherein the receptor-specific moiety is specific for the internalizing receptor.

20. A method of inducing cells to internalize a reporter group in vivo, the method comprising
 introducing into the cells a nucleic acid encoding an internalizing transferrin receptor and
 contacting the cells with a reporter complex comprising a moiety that specifically binds to the introduced internalizing transferrin receptor and the reporter group, whereby the moiety binds to the internalizing transferrin receptor and the reporter complex is moved into the cell carrying the reporter group.

21. The method of claim 20, wherein the reporter group is a magnetic particle, an optically detectable molecule, or a radioisoptope.

22. The method of claim 20, wherein the reporter group is a magnetic, paramagnetic, or superparamagnetic particle.

23. The method of claim 20, wherein the reporter group is a cross-linked dextran coated iron oxide nanoparticle (CLIO).

24. The method of claim 20, wherein the reporter group is a monocrystalline iron oxide nanoparticle (MION).

25. The method of claim 20, wherein the reporter complex further comprising a linker molecule that connects the receptor-specific moiety to the reporter group.

26. The method of claim 20, wherein the cells are located within a subject, and the reporter complex is administered to the subject systemically.

27. The method of claim 26, wherein the reporter complex is injected into the subject intravenously.

* * * * *